United States Patent
Yamato et al.

(10) Patent No.: US 9,836,842 B2
(45) Date of Patent: Dec. 5, 2017

(54) IMAGE PROCESSING APPARATUS AND IMAGE PROCESSING METHOD

(71) Applicant: KONICA MINOLTA, INC., Tokyo (JP)

(72) Inventors: Hiroshi Yamato, Amagasaki (JP);
Kenta Shimamura, Takatsuki (JP);
Osamu Toyama, Kakogawa (JP);
Shintaro Muraoka, Hachioji (JP); Sho Noji, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 192 days.

(21) Appl. No.: 14/433,132

(22) PCT Filed: Sep. 6, 2013

(86) PCT No.: PCT/JP2013/074074
§ 371 (c)(1),
(2) Date: Apr. 2, 2015

(87) PCT Pub. No.: WO2014/054379
PCT Pub. Date: Apr. 10, 2014

(65) Prior Publication Data
US 2015/0254852 A1    Sep. 10, 2015

(30) Foreign Application Priority Data
Oct. 4, 2012 (JP) .................................. 2012-221999

(51) Int. Cl.
*G06K 9/00* (2006.01)
*G06T 7/00* (2017.01)
(Continued)

(52) U.S. Cl.
CPC .......... *G06T 7/0016* (2013.01); *A61B 6/5288* (2013.01); *A61B 6/541* (2013.01);
(Continued)

(58) Field of Classification Search
None
See application file for complete search history.

(56) References Cited

U.S. PATENT DOCUMENTS 5,982,953 A * 11/1999 Yanagita ............... G06F 19/321
348/580
2007/0086678 A1* 4/2007 Chefd'hotel ......... G06K 9/6289
382/294

(Continued)

FOREIGN PATENT DOCUMENTS

JP    2003-245272 A    9/2003
JP    2004-000411 A    1/2004
(Continued)

OTHER PUBLICATIONS

Toyama et al., "Image Generation Device, Image Generation Method, and Program", WO2009/093693 (Bing Translation), Jul. 30, 2009.*

(Continued)

*Primary Examiner* — David H Chu
(74) *Attorney, Agent, or Firm* — Brinks Gilson & Lione

(57) ABSTRACT

An image processing apparatus includes: a base period extracting unit extracting a first target region period based on a first periodic change being a periodic change of a target region in a base moving image acquired by a base moving image acquiring unit; a reference period extracting unit extracting a second target region period based on a second periodic change being a periodic change of the target region in a reference moving image acquired by a reference moving image acquiring unit; a period adjusting unit performing period adjusting processing of synchronizing, for the first target region period or the second target region period, the first periodic change and the second periodic change with each other at a particular phase; and a display image generating unit generating a display image allowing for (Continued)

comparison between the base moving image and the reference moving image after the period adjusting processing is performed.

19 Claims, 24 Drawing Sheets

(51) Int. Cl.
  *G06T 11/60* (2006.01)
  *A61B 6/00* (2006.01)
(52) U.S. Cl.
  CPC ............... *G06T 11/60* (2013.01); *A61B 6/461* (2013.01); *G06T 2207/10124* (2013.01); *G06T 2207/30061* (2013.01); *G06T 2210/41* (2013.01)

(56) References Cited

U.S. PATENT DOCUMENTS

| | | | | |
|---|---|---|---|---|
| 2008/0049994 A1* | 2/2008 | Rognin | ...................... | G06T 7/35 382/128 |
| 2012/0022367 A1* | 1/2012 | Wong | ................. | A61B 1/00165 600/427 |
| 2013/0004044 A1* | 1/2013 | Ross | ..................... | G06T 7/0016 382/131 |

FOREIGN PATENT DOCUMENTS

| | | |
|---|---|---|
| JP | 2008-206741 A | 9/2008 |
| JP | 2009-291313 A | 12/2009 |
| WO | WO 2009/093693 A1 | 7/2009 |

OTHER PUBLICATIONS

International Search Report in International Application No. PCT/JP2013/074074, dated Oct. 1, 2013, 1 page.

Xu, Xin-Wei, and Doi, Kunio, Medical Physics, vol. 22(5), "Image feature analysis and computer-aided diagnosis: Accurage determination of ribcage boundary in chest radiographs," dated May 1996, pp. 617-626.

Aoki, Hirooki, and Nakajima, Masato, Institute of Electronics, Information, and Communication Engineers conference lecture paper collection, 2001, Information and system society conference lecture paper collection, "Unrestrained Respiration Monitoring for Sleeping Person Using Fiber Grating Vision Sensor," dated Aug. 29, 2008, with English lauguage translation, pp. 320-321.

Nakamori, Nobuyuki, et al., Medical Physics, vol. 17, Issue 3, "Image feature analysis and computer-aided diagnosis in digital radiography: Automated analysis of sizes in heart and lung in chest images," dated May 1990, pp. 342-350.

Office Action dated Jan. 18, 2017 in corresponding Chinese Patent Application No. 201380051962.3, 12 pages, with partial English translation, 8 pages.

Office Action dated Aug. 22, 2017 regarding corresponding Japanese patent application No. 2014-539649, 3 pages, with English translation, 2 pages.

Office Action dated Sep. 15, 2017 regarding Correspondence Chinese patent application No. 20130051962.3, 12 pages with partial English translation, 17 pages.

\* cited by examiner

F I G. 6
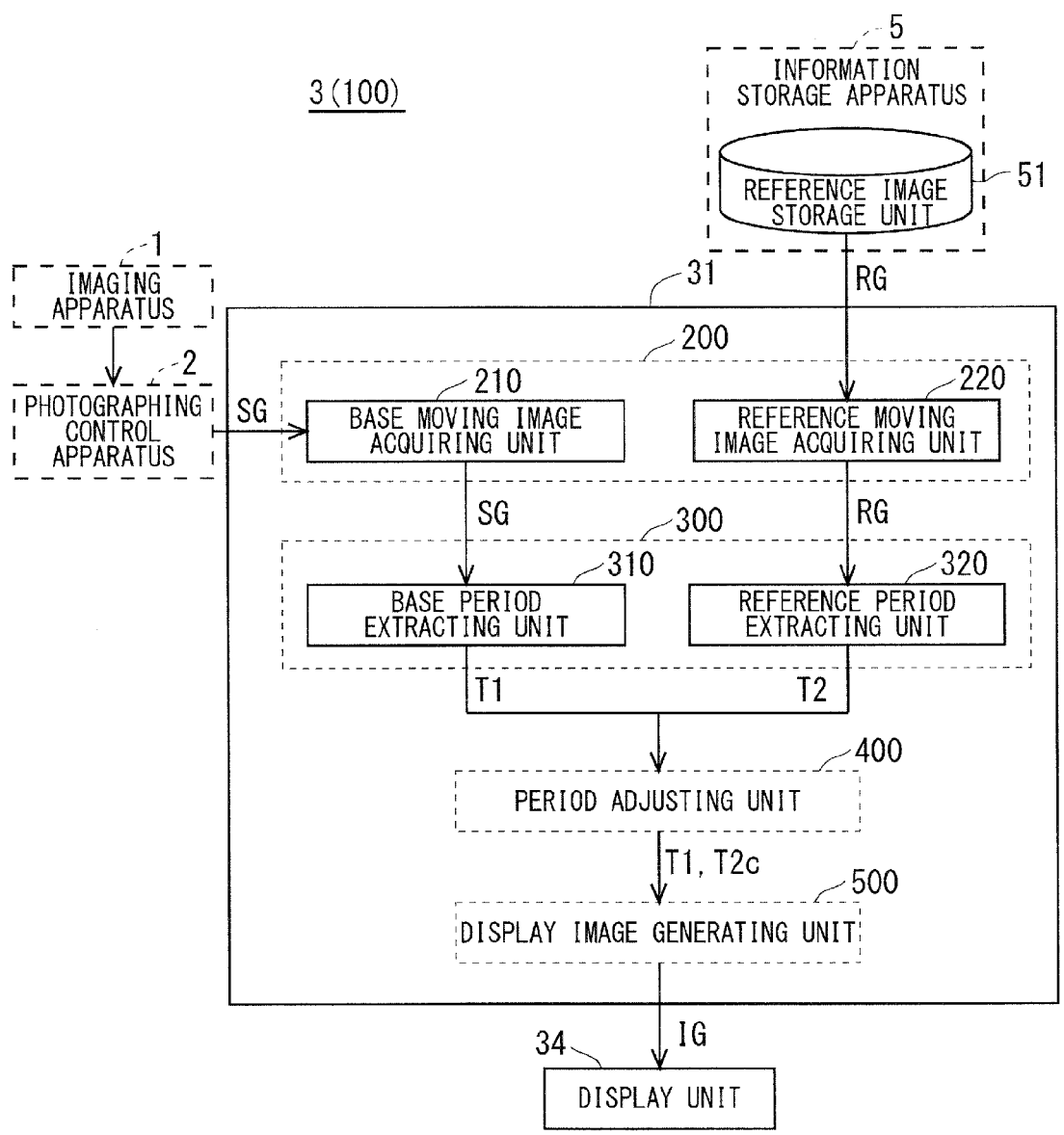

FIG. 8
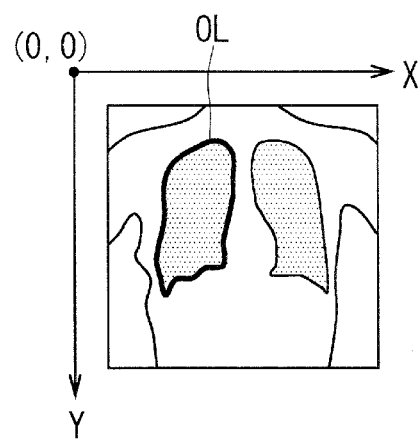
FIG. 9
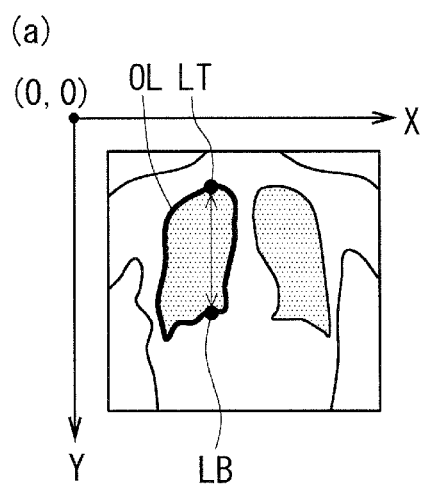
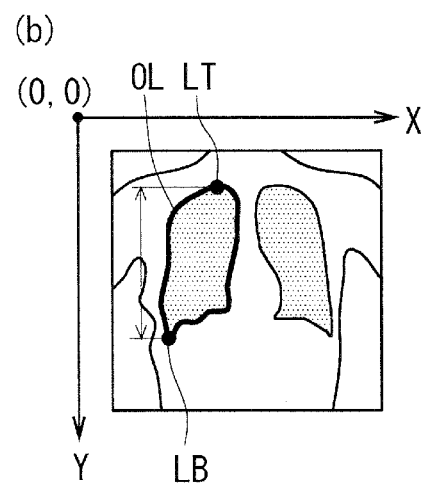

F I G . 1 8
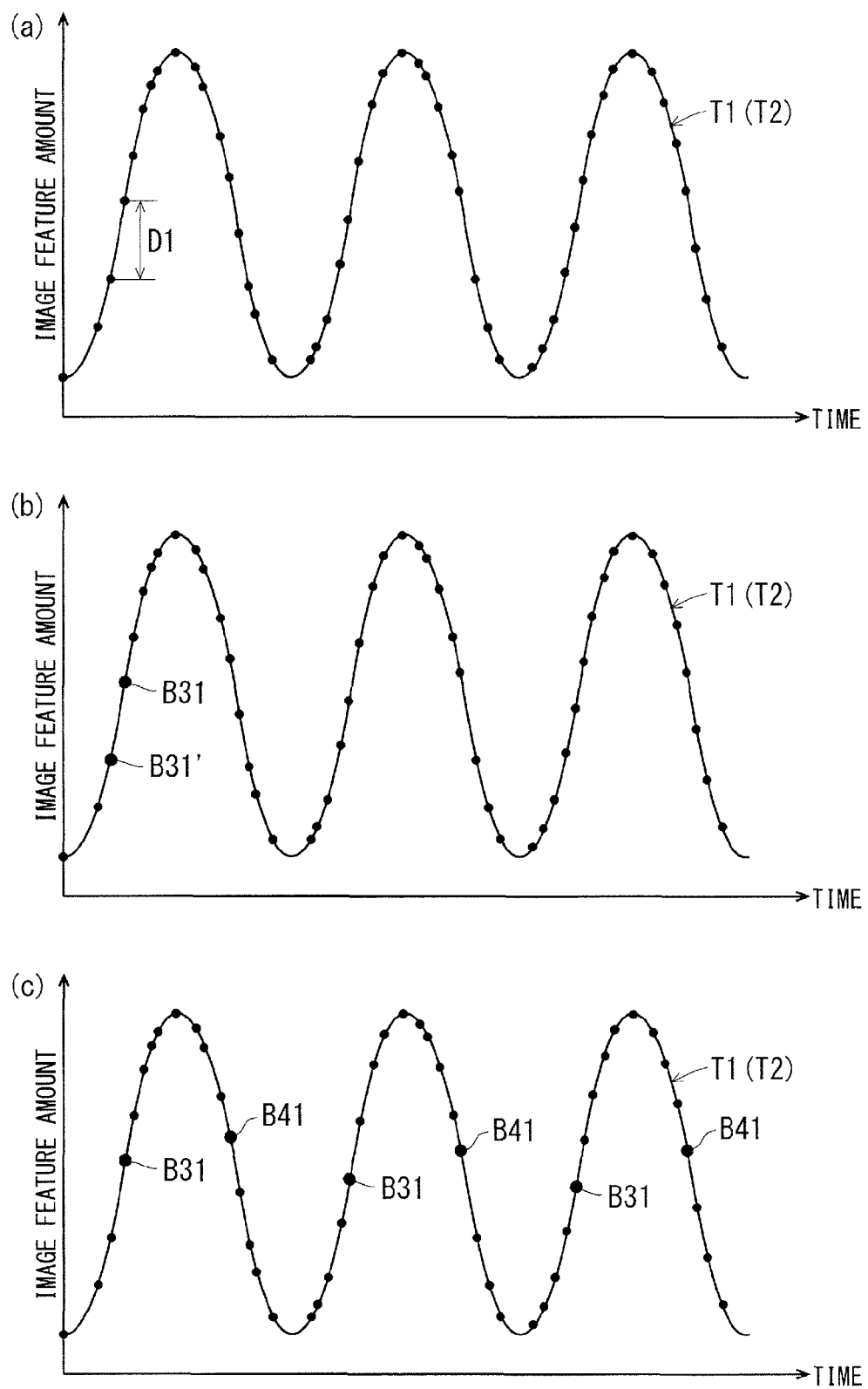

F I G . 1 9
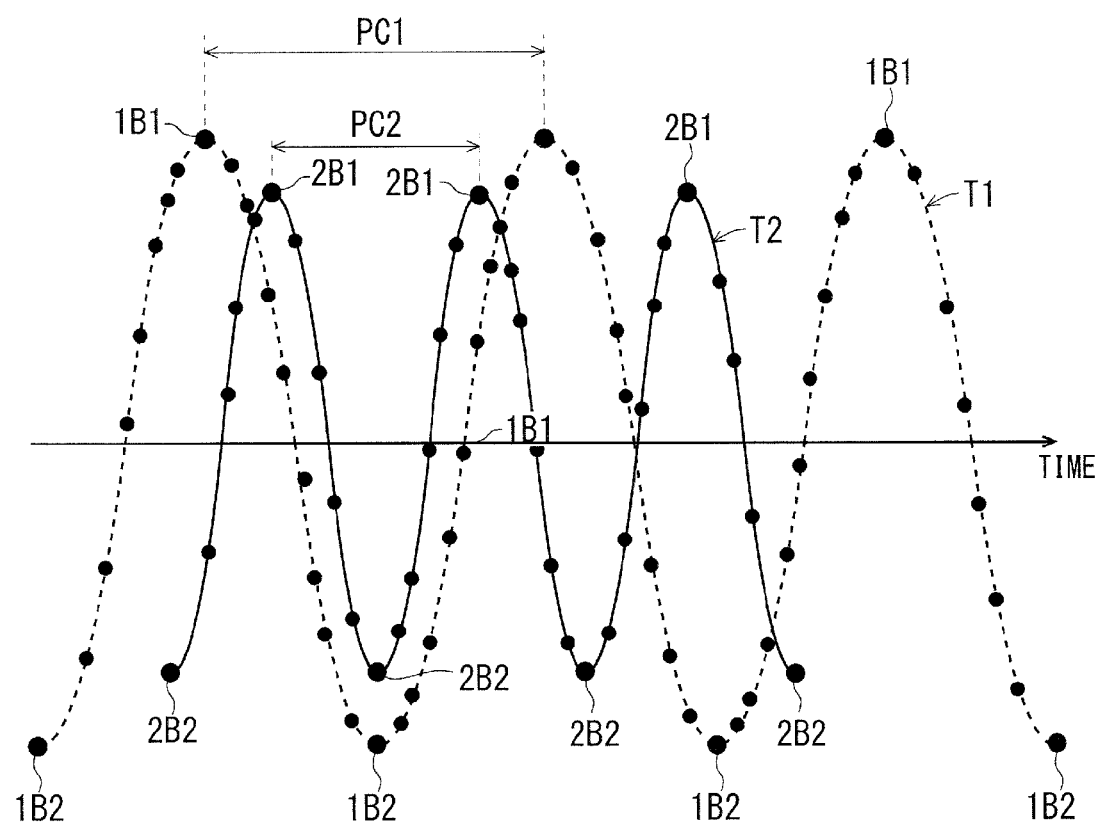

F I G . 2 0
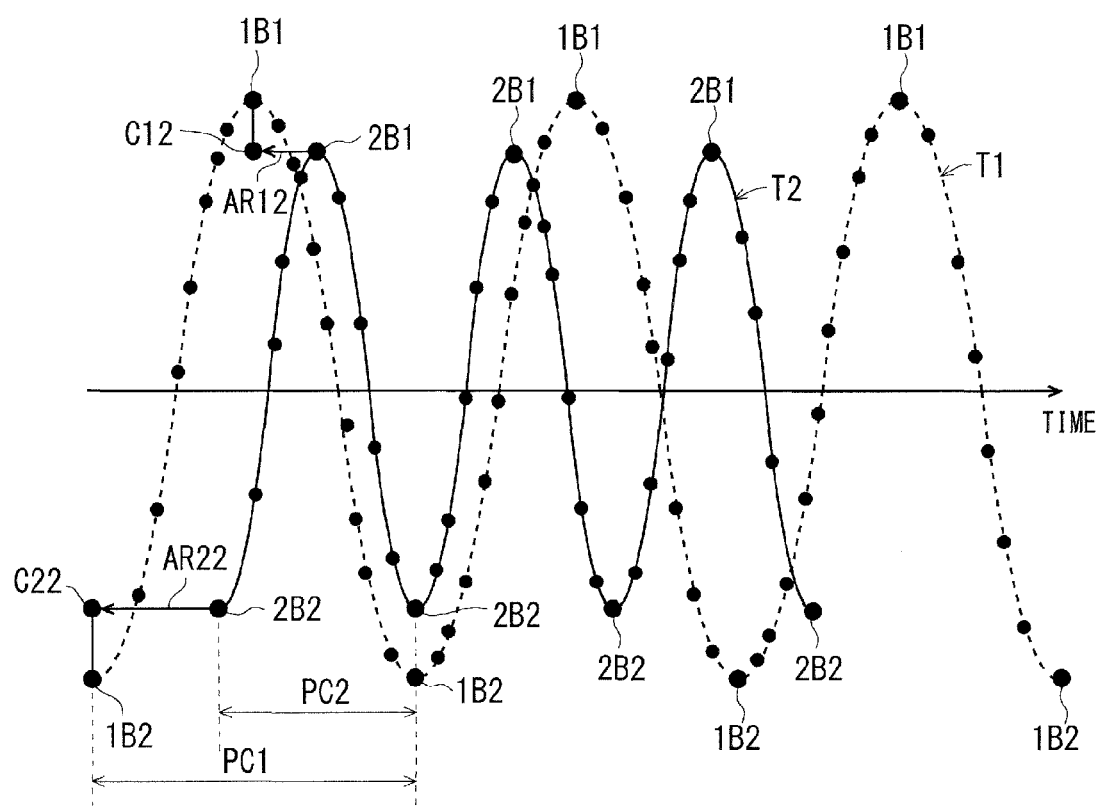

IMAGE PROCESSING APPARATUS AND IMAGE PROCESSING METHOD

This application is a National Stage application of International Application No. PCT/JP2013/074074, filed Sep. 6, 2013.

TECHNICAL FIELD

The present invention relates to image processing technology for displaying a moving image in which a target region of a human body or an animal body is photographed.

BACKGROUND ART

In medical settings, an affected part of a human body or the like in internal organs, skeletons, and the like is photographed, for example, with X-rays for various tests and diagnoses. Through application of recent digital technology, a moving image in which movement of an affected part is captured with X-rays or the like can be acquired relatively easily.

In the recent digital technology, a dynamic image of a subject including a diagnosis target region can be photographed with use of a semiconductor imaging sensor such as a flat panel detector (FPD), enabling diagnosis through motion analysis of the diagnosis target region, which cannot be made in still image photographing and diagnosis by conventional X-ray photography.

In making diagnosis with use of moving images, moving images of the same subject photographed at different times, or moving images of different subjects may be compared with each other, for example. In such cases, it is difficult to simply compare a plurality of moving images because of a phase difference caused by a difference in photographing timing, and a difference in moving speed.

Technology for comparing a plurality of moving images for diagnosis has been proposed in recent years. For example, Patent Document 1. discloses technology of identifying, in moving image displaying technology, a phase of a target object in a series of dynamics, and rearranging frame images constituting a moving image in accordance with the identified phase to display the moving image. Specifically, when moving images of the chest from the front and from the side are displayed side by side, frame images constituting these moving images are rearranged to display these moving images so that phases in these moving images match each other.

Patent Document 2. discloses technology concerning a method of photographing, in radiographic image processing technology, an optical moving image at the same time as a radiographic moving image is photographed, and analyzing movements of test objects in optical moving images to display radiographic moving images so that movements of test objects in the radiographic moving images match each other. Specifically, frame images from which playback of radiographic moving images is started are determined based on movements of test objects, and display intervals between frame images are determined so that the movements of the test objects match each other. When a variation in display intervals between radiographic moving images is equal to or greater than a certain level, an interpolation image is inserted into a radiographic moving image.

PRIOR ART DOCUMENTS

Patent Documents

Patent Document 1: Japanese Patent Application Laid-Open No. 2004-411
Patent Document 2: Japanese Patent Application Laid-Open No. 2008-206741

SUMMARY OF INVENTION

Problems to be Solved by the Invention

Conventional technology disclosed in Patent Document 1. described above has a problem of poor diagnostic performance, as a moving image is processed by rearranging frame images, and is thus different from a series of original frame images.

Conventional technology disclosed in Patent Document 2. described above also has a problem in that, since an artificial interpolation image is inserted into an original moving image, incorrect diagnosis can be made by the presence of the interpolation image.

The present invention has been conceived in view of the above-mentioned matters, and aims to provide image processing technology enabling proper and effective comparison for diagnosis between a plurality of moving images in displaying moving images in which target regions of human bodies or animal bodies are photographed.

Means for Solving the Problems

An image processing apparatus according to the present invention includes: a base moving image acquiring unit acquiring a base moving image in which a periodic change of a physical state of a target region of a human body or an animal is captured; a reference moving image acquiring unit acquiring a reference moving image in which a periodic change of a physical state of the target region of a human body or an animal is captured, the reference moving image being to be compared with the base moving image; a base period extracting unit extracting a first target region period based on a first periodic change that is a periodic change of the target region in the base moving image; a reference period extracting unit extracting a second target region period based on a second periodic change that is a periodic change of the target region in the reference moving image; a period adjusting unit performing period adjusting processing of synchronizing, for the first target region period or the second target region period, the first periodic change and the second periodic change with each other at a particular phase; and a display image generating unit generating a display image allowing for comparison between the base moving image and the reference moving image after the period adjusting processing is performed.

Effects of the Invention

According to the present invention, image processing technology enabling proper and effective comparison for diagnosis between a plurality of moving images in displaying moving images in which target regions of human bodies or animal bodies are photographed can be provided.

These and other objects, features, aspects and advantages of the present invention will become more apparent from the following detailed description and the accompanying drawings.

BRIEF DESCRIPTION OF DRAWINGS

FIG. 6 is a block diagram showing a functional configuration of an image processing apparatus 3 according to Embodiment 1.

FIG. 8 is a schematic diagram illustrating contour extraction of a lung field region.

FIG. 9 is a schematic diagram illustrating positions of feature points of the lung field region.

FIG. 18 is a diagram for explaining a method for detecting a respiratory period.

FIG. 19 is a diagram showing examples of a first lung field region time change T1 and a second lung field region time change T2.

FIG. 20 is a diagram for explaining period adjusting processing.

DESCRIPTION OF EMBODIMENTS

<1. Embodiment 1>

A radiographic dynamic image photographing system according to Embodiment 1. of the present invention is described below.

<1-1. Overall Configuration of Radiographic Dynamic Image Photographing System>

The radiographic dynamic image photographing system according to Embodiment 1. photographs a radiographic dynamic image of a target region of a subject that is a human body or an animal body. The target region includes, for example, lungs and a heart, and is a region whose state changes periodically.

Figure 1:
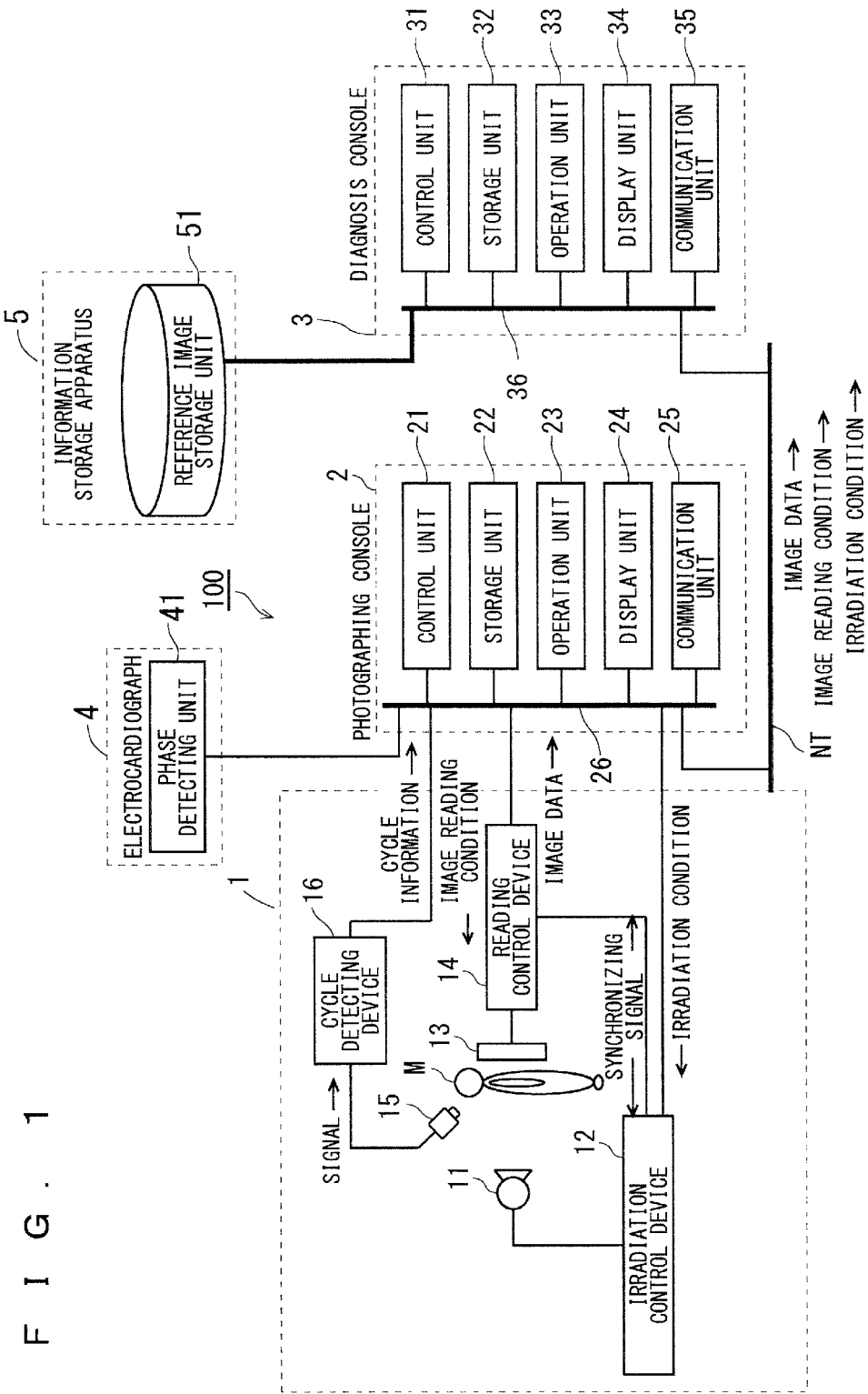
FIG. 1 is a diagram showing an overall configuration of a radiographic dynamic image photographing system 100 according to Embodiment 1.

FIG. 1 is a diagram showing an overall configuration of the radiographic dynamic image photographing system according to Embodiment 1. As shown in FIG. 1, a radiographic dynamic image photographing system 100 includes an imaging apparatus 1, a photographing control apparatus 2 (photographing console), an image processing apparatus 3 (diagnosis console), and an electrocardiograph 4. The imaging apparatus 1 and the electrocardiograph 4 are connected with the photographing control apparatus 2 by a communication cable or the like, and the photographing control apparatus 2 is connected with the image processing apparatus 3 through a communication network NT such as a local area network (LAN). These apparatuses constituting the radiographic dynamic image photographing system 100 comply with the digital image and communications in medicine (DICOM) standard, and communicate with each other in accordance with the DICOM standard.

<1-1-1. Configuration of Imaging Apparatus 1>

The imaging apparatus 1 is configured, for example, by an X-ray imaging apparatus or the like, and photographs dynamics of the chest of a subject M involved in respiration. The dynamics are photographed by acquiring a plurality of images in time sequence while repeatedly irradiating the chest of the subject M with radiation such as X-rays. A series of images acquired through the continuous photographing is referred to as a dynamic image (moving image). The images constituting the dynamic image are each referred to as a frame image.

As shown in FIG. 1, the imaging apparatus 1 includes an irradiation unit (radiation source) 11, an irradiation control device 12, an imaging unit (radiation detecting unit) 13, a reading control device 14, a cycle detecting sensor 15, and a cycle detecting device 16.

The irradiation unit 11 irradiates the subject M with radiation (X-rays) under control of the irradiation control device 12. Illustrated as an example is a system for a human body, and the subject M corresponds to a test target. The subject M is also referred to as a "test subject" below.

The irradiation control device 12 is connected to the photographing control apparatus 2, and controls the irradiation unit 11 based on an irradiation condition input from the photographing control apparatus 2 for radiography.

The imaging unit 13 is configured by a semiconductor imaging sensor such as an FPD, and converts radiation, which has been emitted from the irradiation unit 11 and has passed through the test subject M, into an electrical signal (image information).

The reading control device 14 is connected to the photographing control apparatus 2. The reading control device 14 controls switching units of pixels of the imaging unit 13 based on an image reading condition input from the photographing control apparatus 2 to switch reading of the electrical signals stored in the pixels, and reads the electrical signals stored in the imaging unit 13 to acquire image data. The reading control device 14 then outputs the acquired image data (a frame image) to the photographing control apparatus 2. The image reading condition includes, for example, a frame rate, a frame interval, a pixel size, and an image size (a matrix size). The frame rate is the number of frame images acquired per second, and matches a pulse rate. The frame interval is a time from the start of an operation to acquire one frame image to the start of an operation to acquire the next frame image in continuous photography, and matches a pulse interval.

The irradiation control device 12 and the reading control device 14 are herein connected to each other, and exchange synchronizing signals with each other to synchronize an irradiation operation and an image reading operation with each other.

The cycle detecting device 16 detects a respiratory cycle of the test subject M, and outputs the respiratory cycle to a control unit 21 of the photographing control apparatus 2. The cycle detecting device 16 includes, for example, a cycle detecting sensor 15 that detects movement of the chest of the test subject M (the respiratory cycle of the test subject M) through laser irradiation, and a time measurement unit (not shown) that measures a time of the respiratory cycle detected by the cycle detecting sensor 15 and outputs the time to the control unit 21. In a case where information on the respiratory cycle is acquired from image data as described later, the cycle detecting device 16 can be omitted.

<1-1-2. Configuration of Photographing Control Apparatus 2>

The photographing control apparatus 2 outputs the irradiation condition and the image reading condition to the imaging apparatus 1 to control radiography and a radiographic image reading operation performed by the imaging apparatus 1, and also displays a dynamic image acquired by the imaging apparatus 1 so that a radiographer can check positioning and whether the image is an image suitable for diagnosis or not.

As shown in FIG. 1, the photographing control apparatus 2 includes the control unit 21, a storage unit 22, an operation unit 23, a display unit 24, and a communication unit 25, and these units are connected to one another by a bus 26.

The control unit 21 is configured by a central processing unit (CPU), a random access memory (RAM), and the like. The CPU of the control unit 21 reads a system program and various processing programs stored in the storage unit 22 in response to an operation of the operation unit 23 to develop them in the RAM, and performs various types of processing such as photographing control processing, which is described later, in accordance with the developed program to perform centralized control of an operation of each unit of the photographing control apparatus 2 and an operation of the imaging apparatus 1.

The storage unit 22 is configured by a nonvolatile semiconductor memory, a hard disk, and the like. The storage unit 22 stores various programs to be executed by the control unit 21 and parameters required for the programs to perform processing, or data on processing results, and the like.

The operation unit 23 includes a keyboard including cursor keys, numeric keys, and various function keys, and a pointing device such as a mouse, and outputs an instruction signal input through a key operation made on the keyboard, a mouse operation, or a touch panel to the control unit 21.

The display unit 24 is configured by a monitor such as a color liquid crystal display (LCD), and displays an input instruction, data, or the like from the operation unit 23, in accordance with an instruction of a display signal input from the control unit 21.

The communication unit 25 includes a LAN adapter, a modem, a terminal adapter (TA), and the like, and controls data transmission/reception with each device connected to the communication network NT.

<1-1-3. Configuration of Image Processing Apparatus 3>

The image processing apparatus 3 acquires a dynamic image transmitted from the imaging apparatus 1 through the photographing control apparatus 2, and displays an image to be used by a doctor or the like to make diagnosis through reading.

As shown in FIG. 1, the image processing apparatus 3. includes a control unit 31, a storage unit 32, an operation unit 33, a display unit 34, and a communication unit 35, and these units are connected to one another by a bus 36.

The control unit 31 is configured by a CPU, a RAM, and the like. The CPU of the control unit 31 reads a system program and various processing programs stored in the storage unit 32 in response to an operation of the operation unit 33 to develop them in the RAM, and performs various types of processing in accordance with the developed program to perform centralized control of an operation of each unit of the image processing apparatus 3 (described in detail later).

The storage unit 32 is configured by a nonvolatile semiconductor memory, a hard disk, and the like. The storage unit 32 stores various programs to be executed by the control unit 31 and parameters required for the programs to perform processing, or data on processing results, and the like. For example, the storage unit 32 stores an image processing program for performing image processing, which is described later. These various programs are stored in the form of readable program codes, and the control unit 31 sequentially performs operations according to the program codes.

The operation unit 33 includes a keyboard including cursor keys, numeric keys, and various function keys, and a pointing device such as a mouse, and outputs an instruction signal input through a key operation made on the keyboard, a mouse operation, or a touch panel to the control unit 31.

The display unit 34 is configured by a monitor such as a color LCD, and displays an input instruction and data from the operation unit 33, and a display image, which is described later, in accordance with an instruction of a display signal input from the control unit 31.

The communication unit 35 includes a LAN adapter, a modem, a TA, and the like, and controls data transmission/reception with each device connected to the communication network NT.

<1-1-4. Configuration of Electrocardiograph 4>

Although the electrocardiograph 4 is shown to be apart from the test subject M in FIG. 1, each electrode terminal of the electrocardiograph 4 is actually attached to the test subject M to output an electrocardiographic waveform of the test subject M as a digital signal.

As shown in FIG. 1, the electrocardiograph 4 includes a phase detecting unit 41, and the phase detection unit 41 detects, in response to a control signal from the CPU of the control unit 21, a phase of a heart rate of the subject M as base information for synchronization of photographing operations performed by the imaging apparatus 1. The radiographic dynamic image photographing system 100 according to Embodiment 1 does not necessarily have to include the electrocardiograph 4.

<1-1-5. Configuration of Information Storage Apparatus 5>

As shown in FIG. 1, an information storage apparatus 5 is configured, for example, by a database server including a personal computer or a workstation, includes a reference image storage unit 51, and performs data transmission/reception with the control unit 31 through a bus 36. A reference moving image to be compared with a base moving image, which is described later, is stored in advance in the reference image storage unit 51.

<1-2. Problems Arising When Plurality of Moving Images are Compared>

The following describes problems arising when a plurality of moving images are compared for diagnosis, as premises for description of details of the image processing apparatus 3 in the present embodiment. A case where a previously-photographed moving image and a newly-photographed moving image concerning a lung region are compared is described as an example.

FIGS. 2-5 are diagrams for explaining problems arising when a plurality of moving images are compared. In these diagrams, OT represents movement of a lung region (respiratory cycle) in the previously-photographed moving image, and NT represents the respiratory cycle in the newly-photographed moving image.

Figure 2:
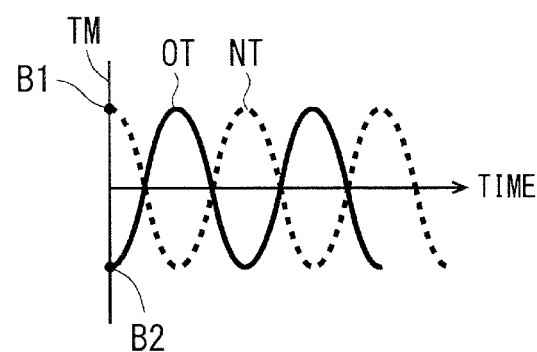
FIG. 2 is a diagram for explaining a problem arising when moving images are compared for diagnosis.

FIG. 2 is a diagram for explaining a difference in respiratory phase caused by a difference in photographing start timing. That is to say, a photographing start timing TM is a timing of maximum exhalation B2 in the respiratory cycle OT in the previous moving image, but is a timing of maximum inhalation B1 in the respiratory cycle NT in the new moving image. Respiratory phases in the two moving images differ in a time direction. It is difficult to compare the moving images if they are displayed without undergoing any processing, as their periods differ by a half-period even though times required for one period are the same.

Figure 3:
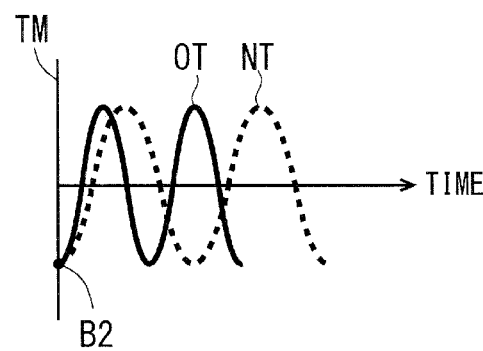
FIG. 3 is a diagram for explaining a problem arising when moving images are compared for diagnosis.

FIG. 3 is a diagram for explaining a difference in respiratory period caused by a difference in respiratory speed. That is to say, the photographing start timing TM is the timing of maximum exhalation B2 both in the respiratory cycle OT in the previous moving image and in the respiratory cycle NT in the new moving image, but the respiratory cycle NT in the new moving image proceeds only by one period while the respiratory cycle OT in the previous moving image proceeds by 1.5. period, and, consequently, the periods differ because of a difference in respiratory speed. If respiratory periods differ as described above, it is difficult to compare the moving images when they are displayed without undergoing any processing.

Figure 4:
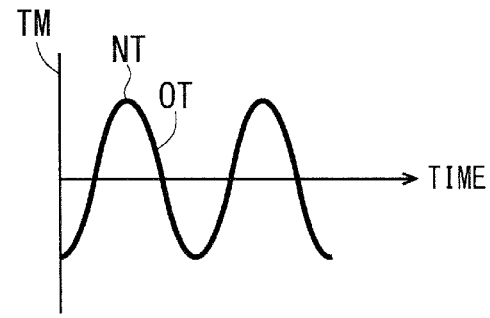
FIG. 4 is a diagram for explaining a problem arising when moving images are compared for diagnosis.

To address the problem shown in FIG. 3, FIG. 4 shows a case where a frame rate is adjusted so that the respiratory periods in the moving images match each other. That is to say, the difference in respiratory period shown in FIG. 3 can be eliminated by extending the period of the respiratory cycle OT in the previous moving image as shown in FIG. 4. Extension of the period of the respiratory cycle OT in the previous moving image can be achieved by insertion of an interpolation image into the previous moving image. The presence of the interpolation image, however, can cause incorrect diagnosis, as described previously.

Figure 5:
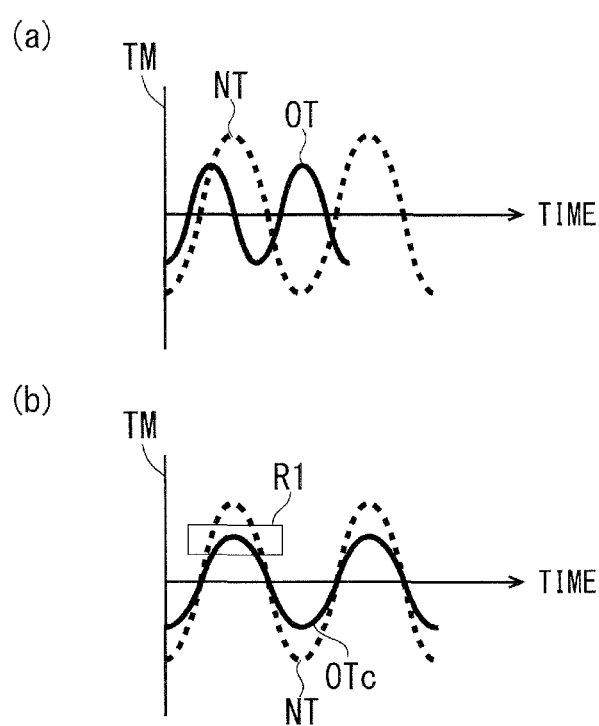
FIG. 5 is a diagram for explaining a problem arising when moving images are compared for diagnosis.

When the respiratory cycle OT in the previous moving image and the respiratory cycle NT in the new moving image have different amplitudes as shown in part (a) of FIG. 5, even if a previous moving image having a respiratory cycle OTc is newly generated by extending the period of the respiratory cycle OT in the previous moving image through insertion of an interpolation image so that times required for one period of the respiratory cycle NT and of the respiratory cycle OTc are the same as shown in part (b) of FIG. 5, the previous moving image can make a different movement from an original movement. This means that, in a region R1 shown in part (b) of FIG. 5, the previous moving image can make a different movement from an actual movement. In a case where comparison between movements themselves is required for diagnosis, display of a different movement from an actual movement can cause an adverse effect (misdiagnosis).

Against this backdrop, it is desired to reduce occurrence of a different movement from an actual movement in a target region during display when a plurality of moving images are compared.

To this end, in the present embodiment, a plurality of moving images are displayed so that movements of target regions in the moving images synchronize with each other for each period even in a case where image display factors, such as periods and phases of the movements of the target regions, differ between the moving images. The plurality of moving images can thus properly and easily be compared with each other, and proper and effective diagnosis of dynamics can be made.

The following describes details of the image processing apparatus 3 in Embodiment 1.

<1-3. Specific Configuration of Image Processing Apparatus 3>

The image processing apparatus 3 of the radiographic dynamic image photographing system 100 in Embodiment 1. of the present invention displays moving images so that changes of target regions in the moving images synchronize with each other for each period even in a case where periodic movements (changes) of the target regions differ between the moving images. As a result, proper and effective diagnosis of dynamics can be made.

<1-3-1. Functional Configuration of Image Processing Apparatus 3>

FIG. 6 shows a functional configuration achieved by the control unit 31 through operation of the CPU and the like in accordance with various programs in the image processing apparatus 3 in the radiographic dynamic image photographing system 100, as well as other configurations. As shown in FIG. 6, the photographing control apparatus 2 is disposed between the imaging apparatus 1 and the image processing apparatus 3, and detected data (a frame image) stored in the storage unit 22 of the photographing control apparatus 2 is output to the communication unit 35 of the image processing apparatus 3 through the communication unit 25. The image processing apparatus 3 in the present embodiment uses a dynamic image in which the chest mainly including the heart and both lungs is photographed.

The control unit 31 is mainly composed of a moving image acquiring unit 200, a period extracting unit 300, a period adjusting unit 400, and a display image generating unit 500.

Although the following description is made on the assumption that the functional configuration of the control unit 31 as shown in FIG. 6 is achieved through execution of a program installed in advance, the functional configuration may be achieved by a dedicated hardware configuration.

The details of processing performed by the moving image acquiring unit 200, the period extracting unit 300, the period adjusting unit 400, and the display image generating unit 500 are sequentially described with reference to FIG. 6.

<1-3-1-1. Moving Image Acquiring Unit 200>

The moving image acquiring unit 200 includes: a base moving image acquiring unit 210 acquiring a base moving image that has been photographed by the reading control device 14 of the imaging apparatus 1 and in which a periodic change of a physical state of a target region of a human body or an animal is captured; and a reference moving image acquiring unit 220 acquiring, from the reference image storage unit 51 of the information storage apparatus 5, a reference moving image in which a periodic change of a physical state of the target region of a human body or an animal is captured and that is to be compared with the base moving image.

The target region in the present embodiment is a chest region including the lungs and the heart, and, in particular, a lung field region is intensively analyzed. The term "physical state" used herein refers to a geometric shape of the lungs and the heart, and includes blood concentration (the presence or absence of blood flow) and the like. In a case where the base moving image is a newly-photographed moving image (a moving image currently targeted for diagnosis), the reference moving image is a previously-photographed moving image of the same person, a model moving image prepared in advance (e.g., an average moving image and a moving image showing a particular case), or the like. The base moving image and the reference moving image may be moving images of the same person photographed from different directions (e.g., from the front and from the side).

The reference moving image in the present embodiment is one moving image or two or more moving images stored in the reference image storage unit 51, and one of the moving images is selected and used by a user.

Figure 7:
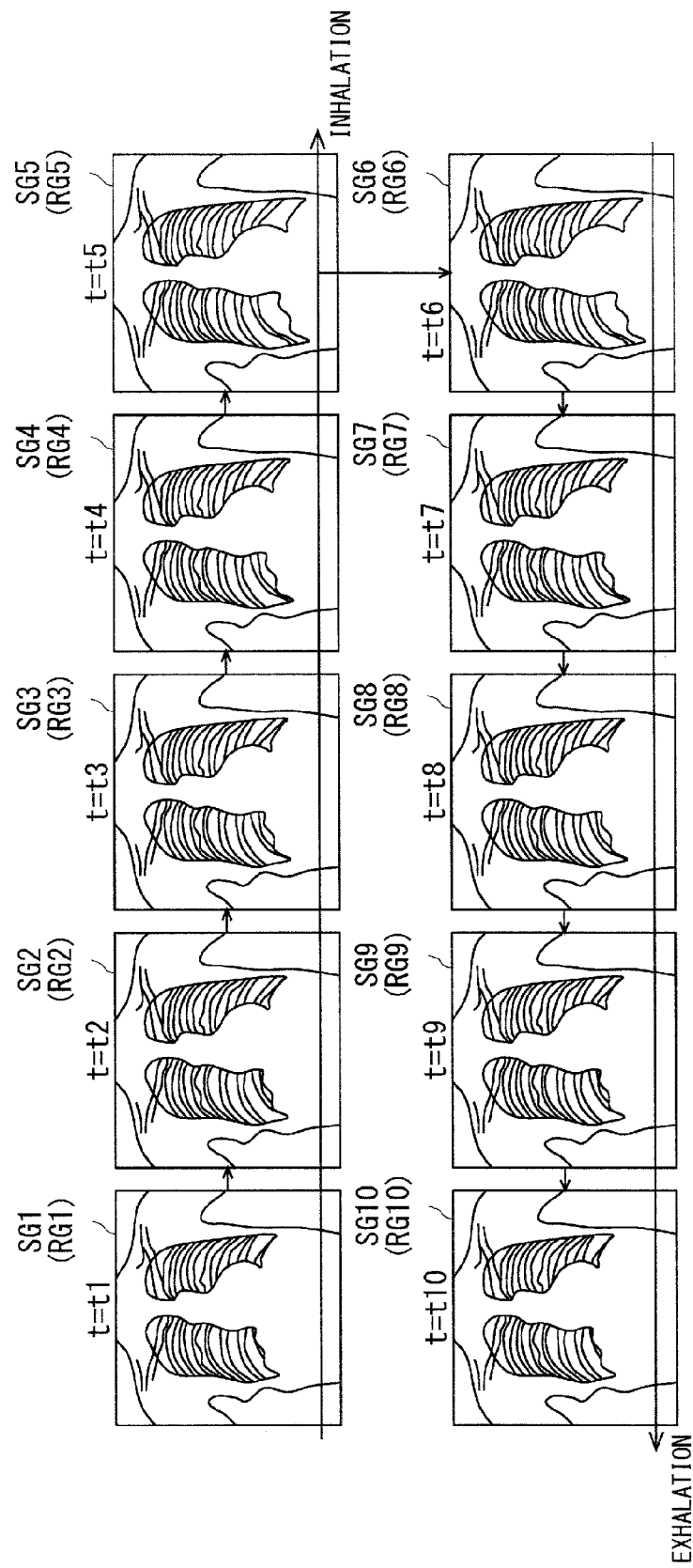
FIG. 7 is a diagram illustrating a dynamic image captured through radiographic dynamic image photography.

FIG. 7 is a diagram illustrating a moving image captured, as for dynamics of the chest of the subject M involved in respiration, through radiographic dynamic image photography. As illustrated in FIG. 7, frame images SG1-SG10 (RG1-RG10) acquired by the base moving image acquiring unit 210 (or the reference moving image acquiring unit 220) are images obtained by consecutively photographing at least one period of the respiratory cycle at constant photographing timings. Specifically, images photographed at photographing timings indicated by a time t=t1, t2, t3, . . . , t10 correspond to the frame images SG1, SG2, SG3, . . . , SG10 (RG1, RG2, RG3, . . . , RG10), respectively.

<1-3-1-2. Period Extracting Unit 300>

The period extracting unit 300 includes: a base period extracting unit 310 detecting a first target region period PC1 based on a periodic change (respiratory cycle) T1 of a target region (lung field) captured in the base moving image (composed of a plurality of base frame images SG), and classifying the plurality of base frame images SG into first target region period PC1 units; and a reference period extracting unit 320 detecting a second target region period PC2 based on a periodic change (respiratory cycle) T2 of the target region (lung field) captured in the reference moving image (composed of a plurality of reference frame images RG), and classifying the plurality of reference frame images RG into second target region period PC2 units (see FIG. 6). The base period extracting unit 310 does not necessarily have to have the function of classifying the plurality of base frame images SG into the first target region period PC1 units, and the reference period extracting unit 320 does also not necessarily have to have the function of classifying the plurality of reference frame images RG into the second target region period PC2 units.

<1-3-1-2-1. First Method for Detecting Change (Respiratory Cycle) of Lung Field Region>

In the present embodiment, a method for detecting a respiratory cycle through analysis of frame images constituting a moving image is used as a method for detecting a change (respiratory cycle) of a lung field region (first detection method). As shown in FIG. 6, the base period extracting unit 310 detects a first respiratory cycle T1 by calculating an area of the lung field region with use of the plurality of base frame images SG acquired by the base moving image acquiring unit 210. Similarly, the reference period extracting unit 320 detects a second respiratory cycle T2 by calculating an area of the lung field region with use of the plurality of reference frame images RG acquired by the reference moving image acquiring unit 220. The area of the lung field region can be obtained by extracting a contour of the lung field region, and defining the number of pixels in a region enclosed by the contour as the lung field region.

FIG. 8 is a schematic diagram illustrating contour extraction of the lung field region. The lung field region may be extracted for each of a left lung field region and a right lung field region as illustrated in FIG. 8, or may be extracted as a contour including regions of the heart and the spine. Conventional technology (see, for example, "Image feature analysis for computer-aided diagnosis: Accurate determination of ribcage boundary in chest radiographs", Xin-Wei Xu and Kunio Doi, Medical Physics, Volume 22(5), May 1995, pp.617-626) may be used as the extraction method.

As described above, the base period extracting unit 310 (reference period extracting unit 320) extracts a contour OL of the lung field region with use of the plurality of base frame images SG (plurality of reference frame images RG) as acquired, and detects the number of pixels in the extracted region as a feature amount, i.e., the area of the lung field region. A periodic change of the area is the first respiratory cycle T1 (second respiratory cycle T2).

As a modification, a distance between feature points of the lung field region may be obtained instead of obtaining the area of the lung field region as described above. In this case, the distance between the feature points of the lung field region can be calculated with use of the plurality of base frame images SG (plurality of reference frame images RG) to generate respiratory information. That is to say, the feature amount is calculated by extracting the lung field region by a similar method to the above-mentioned method, obtaining two feature points from the extracted region, and obtaining a distance between the two points.

FIG. 9 is a diagram illustrating positions of the feature points of the lung field region in the present modification. In a case where a change in length (lung field length) between an upper end LT to a lower end LB of a lung region is calculated, part (a) of FIG. 9 shows an example in which extraction is performed on the assumption that an apical portion of the lung is the upper end LT of the lung region and an intersection of a straight line drawn from the apical portion of the lung in a body axis direction and the diaphragm is the lower end LB of the lung region, and part (b) of FIG. 9 shows an example in which extraction is performed on the assumption that the apical portion of the lung is the upper end LT of the lung region and the costophrenic angle is the lower end LB of the lung region. As described above, the distance between the feature points of the lung field region may be used as the feature amount, and a periodic change of the feature amount may be used as the respiratory cycle.

Figure 10:
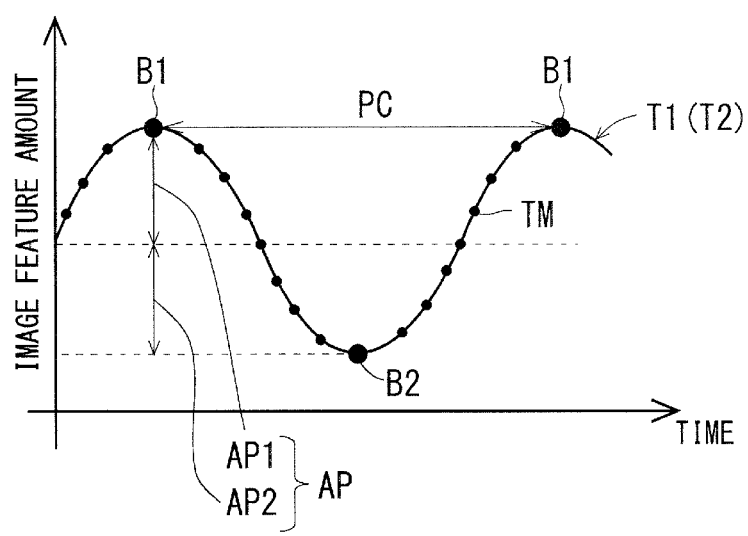
FIG. 10 is a schematic diagram showing waveform data of respiratory information in time sequence.

FIG. 10 is a schematic diagram showing, in time sequence, waveform data of the respiratory information detected by the base period extracting unit 310 (reference period extracting unit 320) in the present embodiment, and shows results of calculation of the feature amount, such as the area of the lung field region, and monitoring of the feature amount in a time direction. As shown in FIG. 10, one period PC of a periodic change of respiration (respiratory cycle) B is composed of inhalation and exhalation, i.e., one exhalation and one inhalation. In inhalation, a region of the lung field in the thoracic cage becomes larger as the diaphragm descends for inhalation. A time of inhalation to a maximum extent (a point at which inhalation is changed to exhalation) is a time of maximum inhalation B1. In exhalation, the region of the lung field becomes smaller as the diaphragm ascends for exhalation, and a time of exhalation to a maximum extent (a point at which exhalation is changed to inhalation) is a time of maximum exhalation B2.

In the present description, a value at which an amplitude value of an image feature amount is the highest is referred to as a maximum amplitude value AP1, a value at which the amplitude value is the lowest is referred to as a minimum amplitude value AP2, and the maximum amplitude value AP1 and the minimum amplitude value AP2 are collectively referred to as an amplitude value AP. A point representing the maximum amplitude value AP1 corresponds to a point of maximum inhalation B1, at which inhalation is changed to exhalation, and a point representing the minimum amplitude value AP2 corresponds to a point of maximum exhalation B2, at which exhalation is changed to inhalation.

As described above, the base period extracting unit 310 (reference period extracting unit 320) detects the first respiratory cycle T1 (second respiratory cycle T2) by extracting the contour OL of the lung field region with use of the plurality of base frame images SG (plurality of reference frame images RG) as acquired, and detecting the area of the lung field region from the extracted region.

<1-3-1-2-2. Second Method for Detecting Change (Respiratory Cycle) of Lung Field Region>

As another modification of the method for detecting the respiratory cycle, the following describes a second method for detecting the respiratory cycle that can be used in place of the above-mentioned first method for detecting the respiratory cycle.

In the second detection method, measurement results obtained by separate equipment are used. That is to say, the respiratory information is acquired from an outside source in synchronization with photographing of the plurality of base frame images SG (or the plurality of reference frame images RG), and the respiratory information is stored in association with the base moving image (or the reference moving image) and used.

Since the cycle detecting device 16 is provided in the system configuration (see FIG. 1) in the present embodiment, the cycle detecting device 16 can be used. In this case, the base period extracting unit 310 acquires the plurality of base frame images SG through the base moving image acquiring unit 210, and can also acquire the respiratory information synchronized with the plurality of base frame images SG through the cycle detecting device 16. On the other hand, the reference period extracting unit 320 acquires the plurality of reference frame images RG as well as the respiratory information synchronized with the plurality of reference frame images RG from the reference image storage unit 51 through the reference moving image acquiring unit 220. As for the reference moving image, it is assumed that the respiratory information is acquired by the cycle detecting device 16 at the time of photographing the reference moving image, and is stored in the reference image storage unit 51 in association with the reference moving image.

In the second method for detecting the respiratory cycle, an apparatus as disclosed in Japanese Patent No. 3793102. can be used, for example. A monitoring technique using laser light and a sensor configured by a CCD camera (see, for example, "A study on respiration monitoring of a sleeping person with FG vision sensor", Hirooki Aoki, Masato Nakajima, The Institute of Electronics, Information and Communication Engineers, Society Conference, Proceedings 2001, Information, System Society Conference Report, pp. 320-321, Aug. 29, 2001) and the like can also be used.

Figure 11:
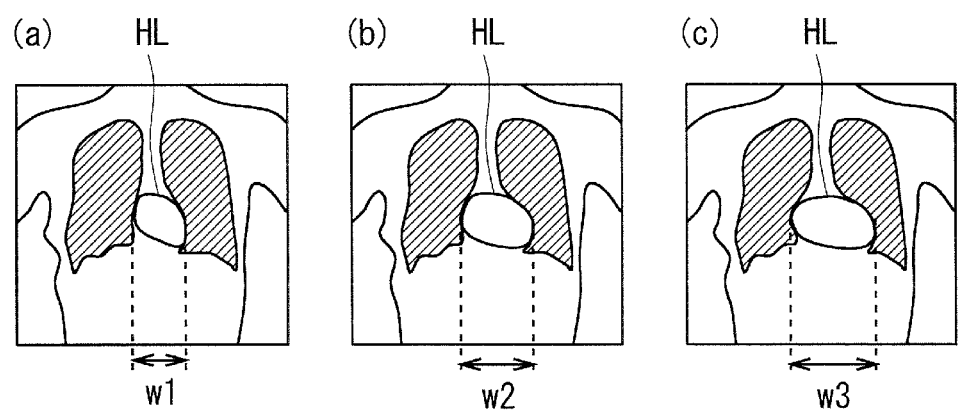
FIG. 11 is a schematic diagram illustrating a change of a cardiac wall.
Figure 12:
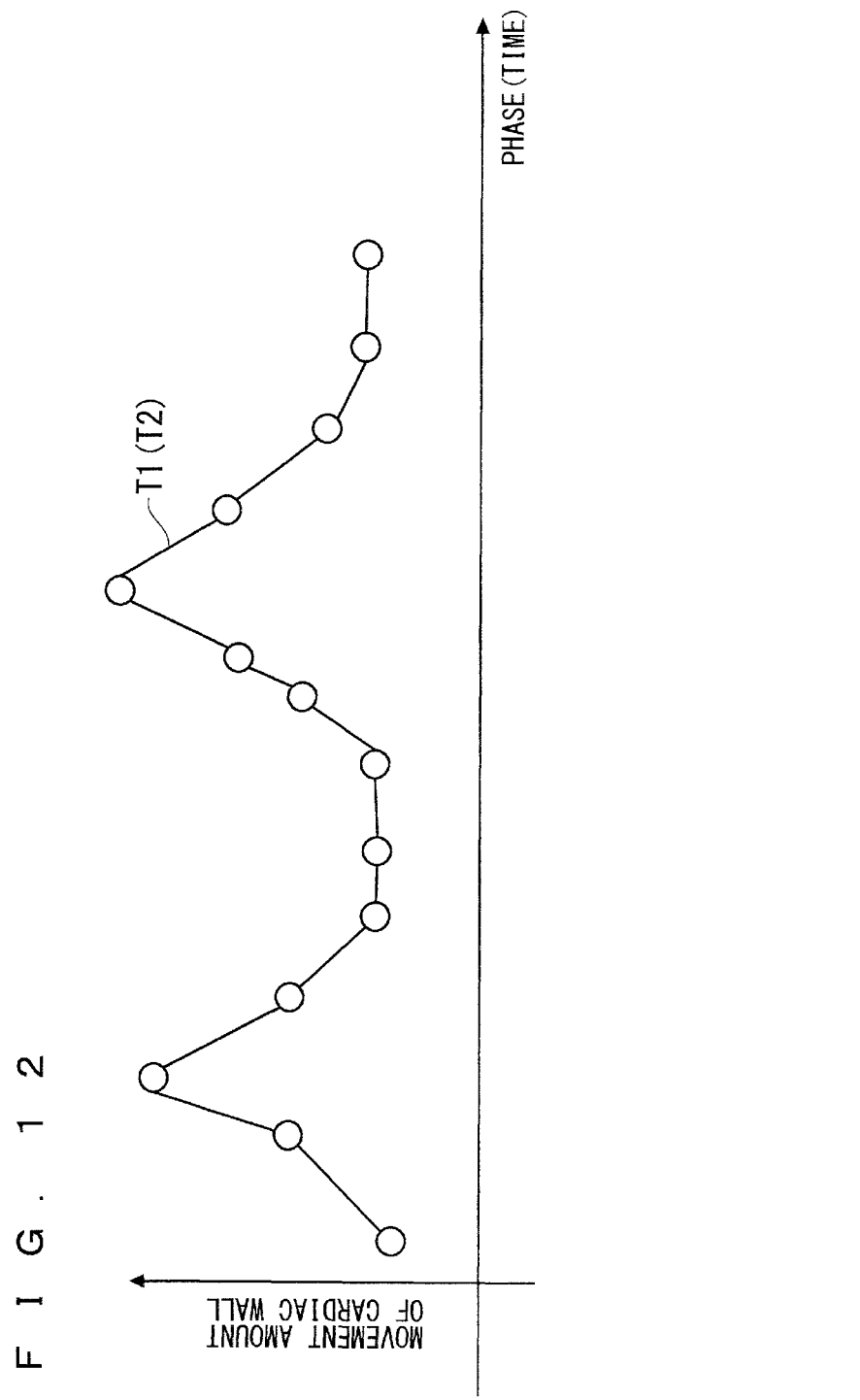
FIG. 12 is a schematic diagram showing an example of a change cycle of the width of a heart.
Figure 13:
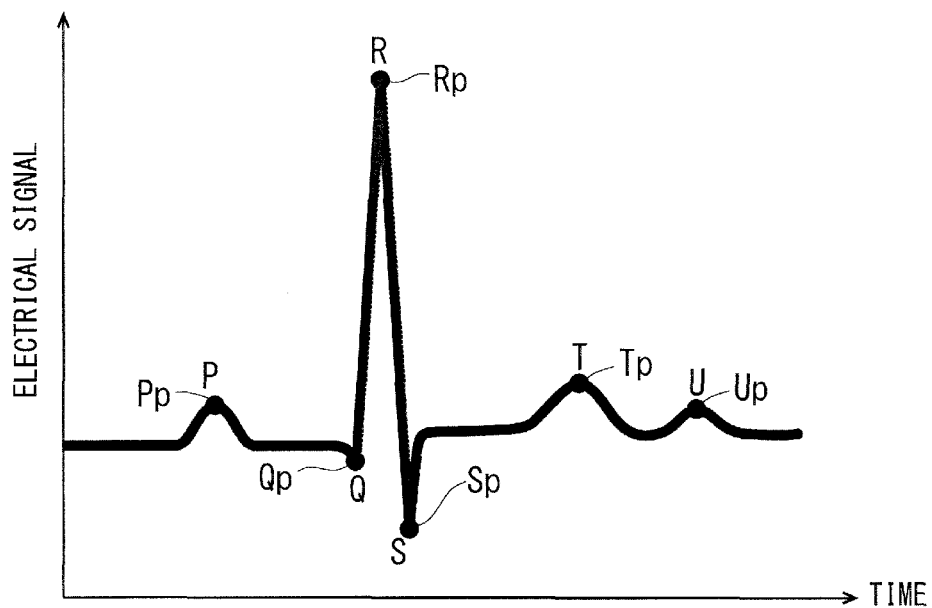
FIG. 13 is a schematic diagram showing an example of a partial waveform measured with an electrocardiograph 4.

Although there is a method of detecting a heart rate cycle (change of a heart region) in place of the respiratory cycle as illustrated in FIGS. 11-13, the heart rate cycle is described in detail later in <Modifications> section.

<1-3-1-2-3. Respiratory Period Detection Method>

The method for detecting the respiratory period based on the first (second) respiratory cycle T1 (T2) is described next. The first respiratory period PC1 or the second respiratory period PC2 can be detected based on: (a1) a timing at which the first respiratory cycle T1 or the second respiratory cycle T2 shows a minimum value within a reference time period and a timing at which the first respiratory cycle T1 or the second respiratory cycle T2 shows a maximum value within the reference time period; (a2) a timing at which a positive or negative sign of an inclination of the first respiratory cycle T1 or the second respiratory cycle T2 changes; (a3) a timing of an inflection point of the first respiratory cycle T1 or the second respiratory cycle T2; (a4) a timing at which the first respiratory cycle T1 or the second respiratory cycle T2 becomes a predetermined threshold; and (a5) a timing at which the absolute value of the inclination of the first respiratory cycle T1 or the second respiratory cycle T2 exceeds a reference value. The first to fifth respiratory period detection methods using these timings (a1) to (a5) are described below. These detection methods may be provided so as to be selectable by a user, or final results may be obtained based on results detected by a plurality of detection methods, for example, through use of an average value. The first respiratory period detection method using the timing (a1) is used in the present embodiment. The second to fifth respiratory period detection methods described below are used in place of or in addition to the first respiratory period detection method.

FIGS. 14-18 are diagrams for explaining the respiratory period detection methods, and show image feature amounts (areas of the lung field regions) in time sequence as in FIG. 10. Black dots represent timings of photographing frame images.

<1-3-1-2-3-1. First Period Detection Method: Maximum Value and Minimum Value>

Figure 14:
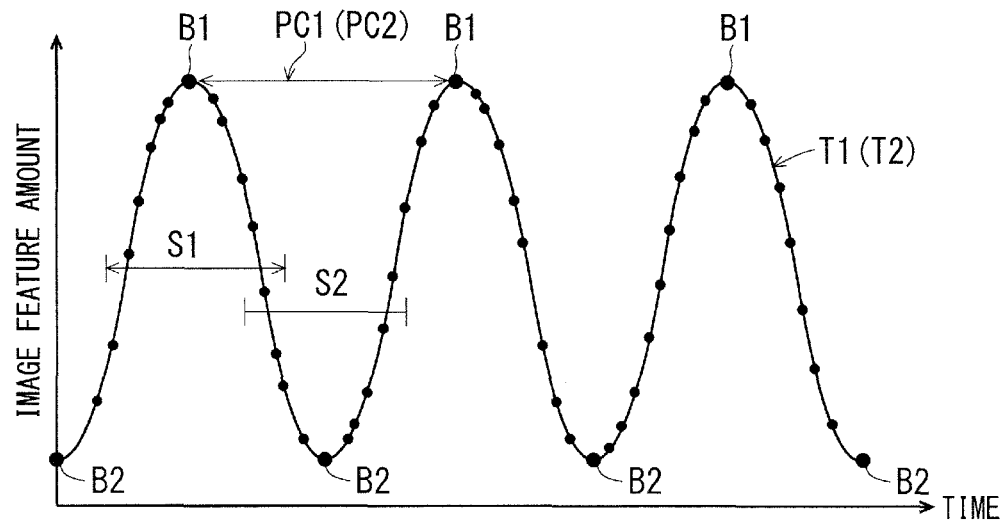
FIG. 14 is a diagram for explaining a method for detecting a respiratory period.

The first period detection method is a detection method based on the timing (a1), which is used in the present embodiment, and the respiratory period is detected based on a maximum value (at the time of maximum inhalation) B1 of the respiratory cycle within a reference time period and a minimum value (at the time of maximum exhalation) B2 of the respiratory cycle within the reference time period. The maximum value and the minimum value herein may be approximate values. That is to say, as shown in FIG. 14, the respiratory period PC1 (PC2) is detected based on a timing showing a maximum value B1 of the first respiratory cycle T1 or the second respiratory cycle T2 within a reference time period S1, or a timing showing a minimum value B2 of the first respiratory cycle T1 or the second respiratory cycle T2 within a reference time period S2. As the reference time period S1 used in search for the maximum value B1, a time period in which there is one maximum amplitude value AP1 (see FIG. 10) (a time period in which the image feature amount is equal to or higher than an average value and has a peak value) is set. As the reference time period S2 used in search for the minimum value B2, a time period in which there is one minimum amplitude value AP2 (see FIG. 10) (a time period in which the image feature amount is equal to or lower than the average value and has a peak value) is set.

The maximum value B1 and the minimum value B2 can be obtained by analyzing the image feature amount as described above, with respect to the plurality of base frame images SG or reference frame images RG. The time of maximum inhalation and the time of maximum exhalation within one period of respiration can be known by taking the maximum value B1 and the minimum value B2 within a range of a certain time period such as the time period S1 and the time period S2. Any of a "period searched in the order of the points B1, B2, and B1", a "period searched in the order of the points B2, B1, and B2", a "period having the points B2 at its two ends (a start point and an end point)", and a "period having the points B1 at its two ends" should be detected as the respiratory period PC1 (PC2). Base frame images SG (reference frame images RG) corresponding to one respiratory period PC1 (PC2) can be classified as frame images for one period.

The first respiratory period PC1 or the second respiratory period PC2 is detected based on the plurality of base frame images SG or reference frame images RG as described above.

<1-3-1-2-3-2. Second Period Detection Method: Positive or Negative Sign of Inclination>

The second period detection method is a detection method based on the timing (a2), and the respiratory period is detected based on a point at which a positive or negative sign of an inclination of the respiratory cycle (a change curve) changes. That is to say, as shown in part (a) of FIG. 15, the respiratory period PC1(PC2) is detected based on change points B10 and B20 at which the positive or negative sign of the inclination of a curve of the first respiratory cycle T1 or the second respiratory cycle T2 changes. Approximate values may be used as the change points B10 and B20.

Figure 15:
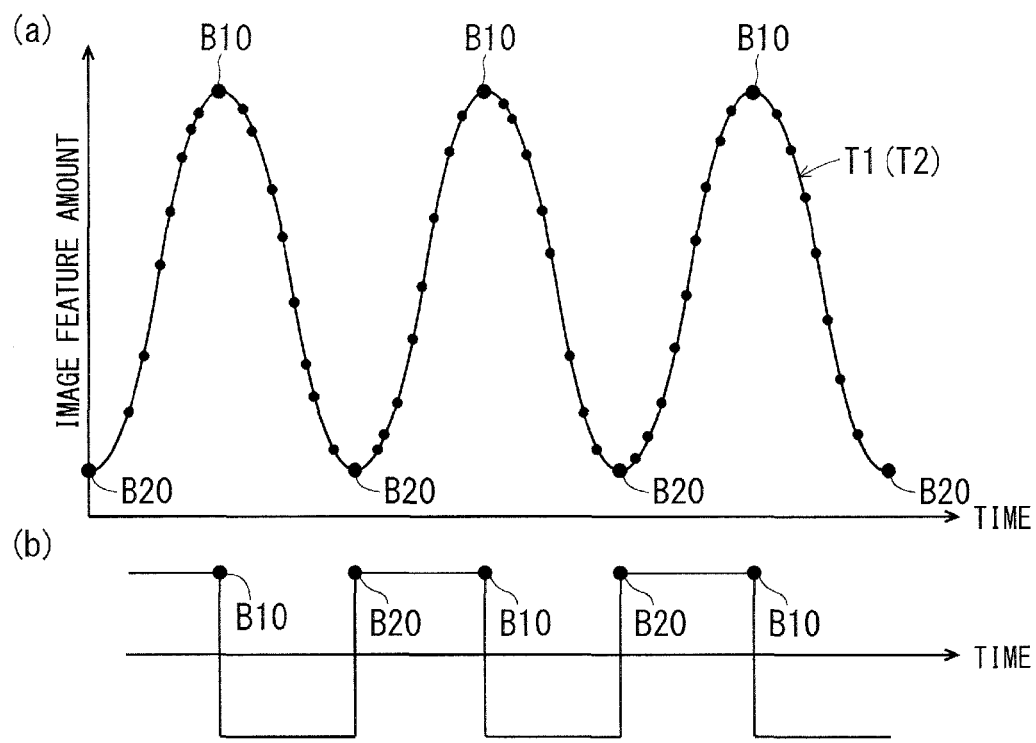
FIG. 15 is a diagram for explaining a method for detecting a respiratory period.

Part (b) of FIG. 15 is a graph showing, when a difference in image feature amount between frame images is obtained in time sequence as for the plurality of base frame images SG or reference frame images RG, whether the difference has a positive sign or a negative sign in accordance with a time axis shown in part (a) of FIG. 15. As shown in part (b) of FIG. 15, the change point B10 at which the difference changes from a positive value to a negative value and the change point B20 at which the difference changes from a negative value to a positive value can be detected by obtaining the difference in image feature amount in time sequence. Any of a "period searched in the order of the change points B10, B20, and B10", a "period searched in the order of the change points B20, B10, and B20", a "period having the change points B20 at its two ends", and a "period having the change points B10 at its two ends" should be detected as the respiratory period. Base frame images SG or reference frame images RG corresponding to one respiratory period are classified as frame images for one period.

Instead of obtaining the difference in image feature amount between frame images in time sequence as described above, a differential value of the curve of the first respiratory cycle T1 or the second respiratory cycle T2 may be obtained.

<1-3-1-2-3-3. Third Period Detection Method: Inflection Point>

Figure 16:
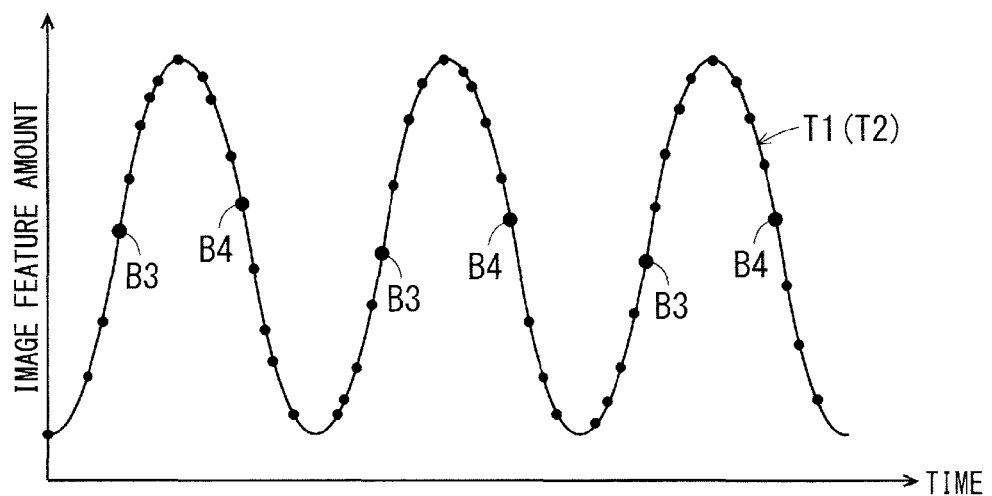
FIG. 16 is a diagram for explaining a method for detecting a respiratory period.

The third period detection method is a detection method based on the timing (a3), and the respiratory period is detected based on an inflection point of the respiratory cycle (change curve). That is to say, as shown in FIG. 16, the respiratory period PC1 (PC2) is detected based on timings showing inflection points B3 and B4 of the first respiratory cycle T1 or the second respiratory cycle T2. Approximate values may be used as the inflection points B3 and B4.

For example, the first respiratory cycle T1 or the second respiratory cycle T2 is expressed by a function on the assumption that the first respiratory cycle T1 or the second respiratory cycle T2 has a period, and points at which concavity or convexity changes, which can be known by obtaining a differential of the function twice, are extracted as inflection points. From among timings of photographing the plurality of base frame images SG or reference frame images RG, photographing timings that are the closest to the inflection points are detected as the inflection points B3 and B4 (see FIG. 16). Any of a "period searched in the order of the inflection points B3, B4, and B3", a "period searched in the order of the inflection points B4, B3, and B4", a "period having the inflection points B4 at its two ends", and a "period having the inflection points B3 at its two ends" should be detected as the respiratory period. Base frame images SG or reference frame images RG corresponding to one respiratory period are classified as frame images for one period.

<1-3-1-2-3-4. Fourth Period Detection Method: Predetermined Threshold>

Figure 17:
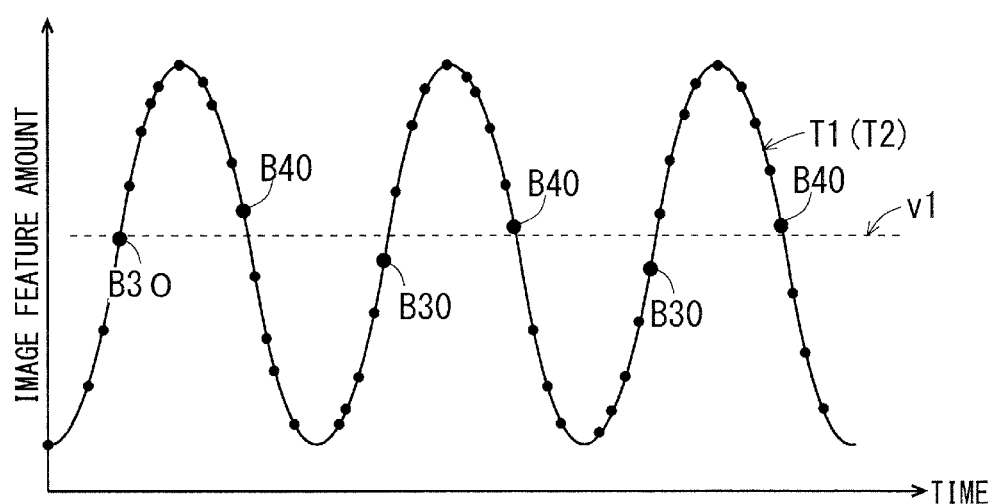
FIG. 17 is a diagram for explaining a method for detecting a respiratory period.

The fourth period detection method is a detection method based on the timing (a4), and the respiratory period is detected based on a timing at which the respiratory cycle becomes a predetermined threshold. That is to say, as shown in FIG. 17, the respiratory period PC1 (PC2) is detected based on points B30 and B40 at which the first respiratory cycle T1 or the second respiratory cycle T2 becomes a certain threshold v1. The threshold v1 herein is preferably an intermediate value of the image feature amount in the first respiratory cycle T1 or the second respiratory cycle T2. The points B30 and B40 may be approximate values.

For example, the first respiratory cycle T1 or the second respiratory cycle T2 is expressed by a function on the assumption that the first respiratory cycle T1 or the second respiratory cycle T2 has a period, and points at which the first respiratory cycle T1 or the second respiratory cycle T2 becomes a certain threshold are detected. From among timings of photographing the plurality of base frame images SG or reference frame images RG, photographing timings that are the closest to the detected points are detected as the points B30 and B40 (see FIG. 17). Any of a "period searched in the order of the points B30, B40, and B30", a "period searched in the order of the points B40, B30, and B40", a "period having the points B40 at its two ends", and a "period having the points B30 at its two ends" should be detected as the respiratory period. Base frame images SG or reference frame images RG corresponding to one respiratory period are classified as frame images for one period.

<1-3-1-2-3-5. Fifth Period Detection Method: Absolute Value of Inclination>

The fifth period detection method is a detection method based on the timing (a5), and the respiratory period is detected based on the absolute value of the inclination of the respiratory cycle (change curve). That is to say, as shown in FIG. 18, the respiratory period PC1 (PC2) is detected based on a timing at which the absolute value of the inclination of the first respiratory cycle T1 or the second respiratory cycle T2 exceeds a reference value. The reference value herein is a maximum possible value of the inclination of the first respiratory cycle T1 or the second respiratory cycle T2, and an empirically-known value and the like can be used.

For example, as in the second period detection method, a difference in image feature amount between frame images is obtained in time sequence as for the plurality of base frame images SG or reference frame images RG, and the difference D1 is set as a value indicating the inclination (when a time interval between frame images is constant, the difference becomes the value indicating the inclination) as shown in part (a) of FIG. 18. As shown in part (b) of FIG. 18, a point B31 (or a point B31') at which the difference D1 exceeds the reference value is obtained (see part (b) of FIG. 18).

In this method, the "absolute value" of the inclination is used to obtain a point at which the difference D1 exceeds the reference value, and thus a point at which the inclination becomes the smallest (a point at which the inclination becomes the largest in a negative direction) is also included. Points B41 are therefore detected in addition to the points B31 as the points at which the absolute value of the difference D1 exceeds the reference value as shown in part (c) of FIG. 18. Any of a "period searched in the order of the points B31, B41, and B31", a "period searched in the order of the points B41, B31, and B41", a "period having the points B41 at its two ends", and a "period having the points B31 at its two ends" should be detected as the respiratory period. Base frame images SG or reference frame images RG corresponding to one respiratory period are classified as frame images for one period.

<1-3-1-3. Period Adjusting Unit 400>

The period adjusting unit 400 performs period adjusting processing of synchronizing, for each first respiratory period (target region period) PC1 or second respiratory period (target region period) PC2, periodic changes of a lung field region (target region) in a base moving image and in a reference moving image with each other at a particular phase. The period adjusting processing can be performed based on a feature point for adjustment that is any one of: (b1) a first feature point at which the first respiratory cycle T1 and the second respiratory cycle T2 are the smallest for each first respiratory period PC1 and second respiratory period PC2; (b2) a second feature point at which the first respiratory cycle T1 and the second respiratory cycle T2 are the largest for each first respiratory period PC1 and second respiratory period PC2; (b3) a third feature point at which the first respiratory cycle T1 and the second respiratory cycle T2 become inflection points for each first respiratory period PC1 and second respiratory period PC2; (b4) a fourth feature point at which the first respiratory cycle T1 and the second respiratory cycle T2 become a predetermined threshold for each first respiratory period PC1 and second respiratory period PC2; and (b5) a fifth feature point at which the absolute values of inclinations of the first respiratory cycle T1 and the second respiratory cycle T2 are the highest for each first respiratory period PC1 and second respiratory period PC2. The feature point for adjustment indicates a particular phase for synchronization.

The period adjusting processing includes processing of setting one of the first respiratory cycle T1 and the second respiratory cycle T2 as a respiratory cycle to be fixed, setting the other one of the first respiratory cycle T1 and the second respiratory cycle T2 as a respiratory cycle to be adjusted as a target for adjustment, and shifting, in a time direction, a timing at which the respiratory cycle to be adjusted becomes the feature point for adjustment so as to match a timing at which the respiratory cycle to be fixed becomes the feature point for adjustment. Since the first respiratory cycle T1 and the second respiratory cycle T2 respectively correspond to the base moving image (composed of the plurality of base frame images SG) and the reference moving image (composed of the plurality of reference frame images RG), shifting the first respiratory cycle T1 or the second respiratory cycle T2 in the time direction means shifting the base moving image or the reference moving image in the time direction. That is to say, display timings of the plurality of base frame images SG or reference frame images RG are changed.

In the present embodiment, in a case where the base moving image is a moving image currently targeted for diagnosis, it is preferable to set the first respiratory cycle T1, which corresponds to the base moving image, as the respiratory cycle to be fixed, and to set the second respiratory cycle T2, which corresponds as the reference moving image, as the respiratory cycle to be adjusted.

Figure 21:
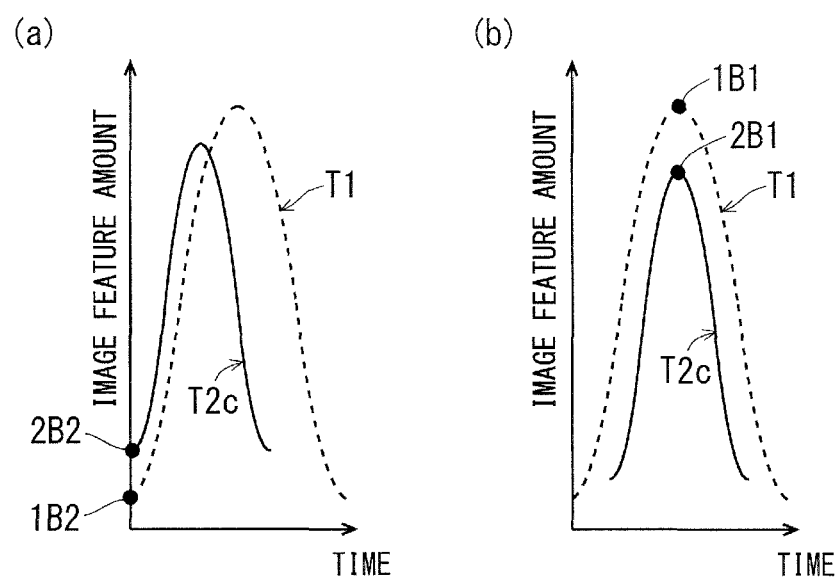
FIG. 21 is a diagram for explaining period adjusting processing.

FIG. 19 is a diagram showing examples of the first respiratory cycle T1 and the second respiratory cycle T2 together. In FIG. 19, a point 1B1 in the first respiratory cycle T1 and a point 2B1 in the second respiratory cycle T2 are points representing the time of maximum inhalation in one period of respiration detected by the above-mentioned first period detection method, and a point 1B2 in the first respiratory cycle T1 and a point 2B2 in the second respiratory cycle T2 are points representing the time of maximum exhalation in one period of respiration detected by the above-mentioned first period detection method (the same applies to FIGS. 20 and 21 described later). As shown in FIG. 19, the period PC1 of the first respiratory cycle and the period PC2 of the second respiratory cycle T2 differ from each other, and thus it is difficult to compare the base moving image and the reference moving image for diagnosis due to a difference in movement when these moving images are displayed simultaneously without undergoing any processing.

To address the problem, the period adjusting unit 400 performs the period adjusting processing for each first respiratory period PC1 or second respiratory period PC2.

FIGS. 20-23 are diagrams for explaining the period adjusting processing.

In the period adjusting processing shown in FIGS. 20-23, the first respiratory cycle T1 is set as the respiratory cycle to be fixed, and the second respiratory cycle T2 is set as the respiratory cycle to be adjusted.

<1-3-1-3-1. Adjustment Method Based on First Feature Point>

FIG. 20 shows a method for performing the period adjusting processing based on the above-mentioned first feature point in the present embodiment. In this adjustment method, the period adjusting processing is performed by setting the points 1B2 and 2B2 at which the first respiratory cycle T1 and the second respiratory cycle T2 are respectively the smallest for each first respiratory period PC1 and second respiratory period PC2 as the feature points for adjustment as shown in FIG. 20.

In this period adjustment method, a timing at which the second respiratory cycle T2 becomes the point 2B2 is shifted in the time direction so as to match a timing at which the first respiratory cycle T1 becomes the point 1B2. That is to say, the points 1B2 and 2B2 at which the image feature amount is the smallest are caused to match each other in the time direction. Specifically, the points 1B2 and 2B2 are caused to match each other in the time direction by shifting the point 2B2 to an adjustment point C22 in a direction of an arrow AR22. This means that a reference moving image corresponding to the second respiratory cycle T2 is displayed at an earlier timing in each respiratory period PC2. As a result, the second respiratory cycle T2 is shifted in the time direction to be a second respiratory cycle T2c as shown in part (a) of FIG. 21. According to this period adjustment method, timings of maximum exhalation can be caused to match each other for each respiratory period PC1 when the base moving image and the reference moving image are displayed.

<1-3-1-3-2. Adjustment Method Based on Second Feature Point>

As the adjustment method based on the second feature point, the period adjusting processing is performed by setting the points 1B1 and 2B1 at which the first respiratory cycle T1 and the second respiratory cycle T2 are respectively the largest for each first respiratory period PC1 and second respiratory period PC2 as the feature points for adjustment as shown in FIG. 20.

In this period adjustment method, a timing at which the second respiratory cycle T2 becomes the point 2B1 is shifted in the time direction so as to match a timing at which the first respiratory cycle T1 becomes the point 1B1. That is to say, this is a method of matching the points 1B1 and 2B1 at which the image feature amount is the largest each other in the time direction. Specifically, the points 1B1 and 2B1 can be caused to match each other in the time direction by shifting the point 2B1 to an adjustment point C12 in a direction of an arrow AR12. This means that the reference moving image corresponding to the second respiratory cycle T2 is displayed at an earlier timing in each respiratory period PC2. As a result, the second respiratory cycle T2 is shifted in the time direction to be a second respiratory cycle T2c as shown in part (b) of FIG. 21. According to this period adjustment method, timings of maximum inhalation can be caused to match each other for each respiratory period PC1 when the base moving image and the reference moving image are displayed.

In the present embodiment, the above-mentioned adjustment method based on the first feature point and the above-mentioned adjustment method based on the second feature point are used, and either one of these two adjustment methods can be selected by a user.

The following describes adjustment methods based on the third to fifth feature points, which are adjustment methods suitable in cases where the above-mentioned third to fifth period detection methods are used.

<1-3-1-3-3. Adjustment Methods Based on Third to Fifth Feature Points (1)>

Figure 22:
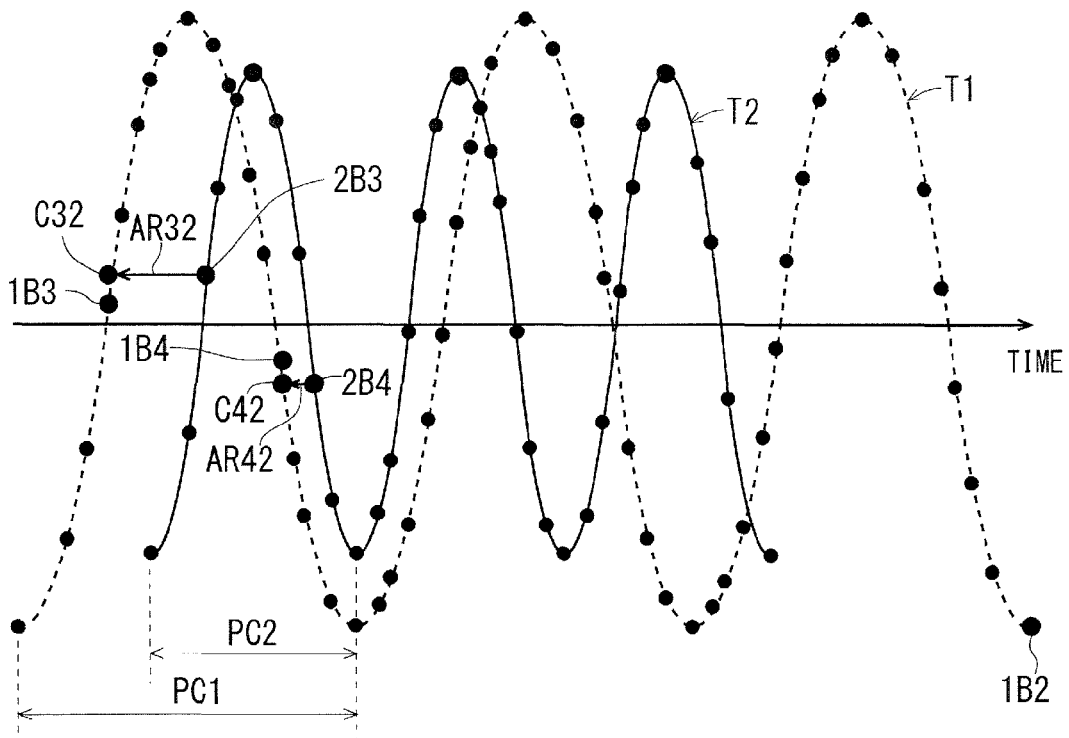
FIG. 22 is a diagram for explaining period adjusting processing.
Figure 23:
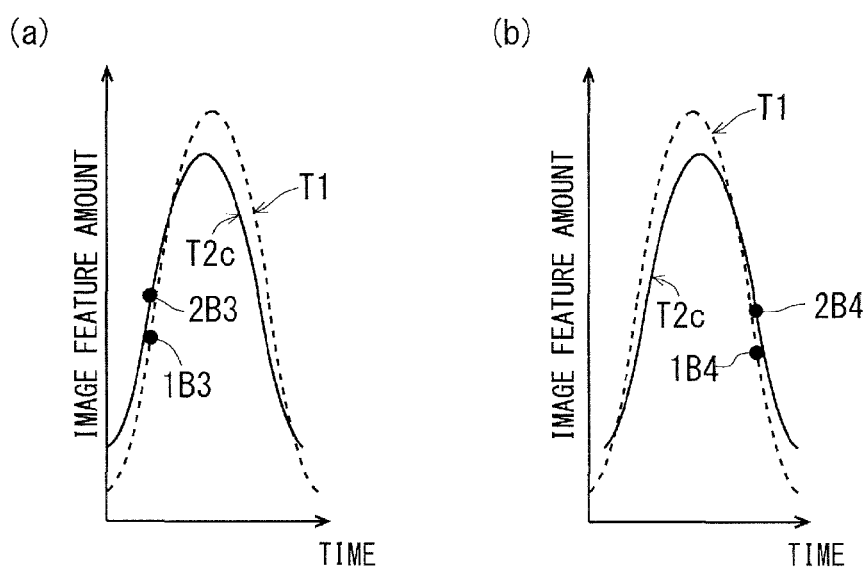
FIG. 23 is a diagram for explaining period adjusting processing.

FIGS. 22 and 23 show adjustment methods based on the above-mentioned third to fifth feature points, and their results. In FIGS. 22 and 23, intermediate points 1B3 and 1B4 in the first respiratory cycle T1 and intermediate points 2B3 and 2B4 in the second respiratory cycle T2 are points detected by the above-mentioned third to fifth period detection methods. In the adjustment methods based on the third to fifth feature points (1), the period adjusting processing is performed by setting the intermediate points 1B3 and 2B3 as feature points for adjustment for each first respiratory period PC1 and second respiratory period PC2 as shown in FIG. 22. The intermediate points 1B3 and 2B3 herein correspond to the inflection points B3 detected by the third period detection method in a case of processing based on the third feature point, correspond to the points B30 that are detected by the fourth period detection method and are obtained based on the certain threshold v1 in a case of processing based on the fourth feature point, and correspond to the points B31 that are detected by the fifth period detection method and at which the inclination is the largest in a case of processing based on the fifth feature point.

In this period adjustment method, a timing at which the second respiratory cycle T2 becomes the intermediate point 2B3 is shifted in the time direction so as to match a timing at which the first respiratory cycle T1 becomes the intermediate point 1B3. That is to say, the intermediate points 1B3 and 2B3 of the image feature amount are caused to match each other in the time direction. Specifically, the intermediate points 1B3 and 2B3 can be caused to match each other in the time direction by shifting the intermediate point 2B3 to an adjustment point C32 in a direction of an arrow AR32 as shown in part (a) of FIG. 23.

<1-3-1-3-4. Adjustment Methods Based on Third to Fifth Feature Points (2)>

In the adjustment methods based on the third to fifth feature points (2), the period adjusting processing is performed by setting the intermediate points 1B4 and 2B4 as feature points for adjustment for each first respiratory period PC1 and second respiratory period PC2 as shown in FIG. 22. The intermediate points 1B4 and 2B4 herein correspond to the inflection points B4 detected by the third period detection method in the case of processing based on the third feature point, correspond to the points B40 that are detected by the fourth period detection method and are obtained based on the certain threshold v1 in the case of processing based on the fourth feature point, and correspond to the points B41 that are detected by the fifth period detection method and at which the inclination is the largest in the case of processing based on the fifth feature point.

In this period adjustment method, a timing at which the second respiratory cycle T2 becomes the intermediate point 2B4 is shifted in the time direction so as to match a timing at which the first respiratory cycle T1 becomes the intermediate point 1B4. That is to say, the intermediate points 1B4 and 2B4 of the image feature amount are caused to match each other in the time direction. Specifically, the intermediate points 1B4 and 2B4 can be caused to match each other in the time direction by shifting the intermediate point 2B4 to an adjustment point C42 in a direction of an arrow AR42 as shown in part (b) of FIG. 23.

<1-3-1-4. Display Image Generating Unit 500>

As described above, in cases of FIGS. 20-23, the second respiratory cycle T2 is shifted in the time direction so as to be the second respiratory cycle T2c, and thus the period adjusting unit 400 outputs the first respiratory cycle T1 and the second respiratory cycle T2c to the display image generating unit 500. The display image generating unit 500 generates a display image IG based on the first respiratory cycle T1 and the second respiratory cycle T2c after the period adjusting processing is performed, and outputs the display image IG to the display unit 34 (see FIG. 6). The display image IG is an image for displaying the base moving image and the reference moving image for comparison, and, in this display, the first respiratory cycle T1 and the second respiratory cycle T2c have undergone the period adjusting processing. In other words, the plurality of base frame images SG constituting the base moving image are each used for the display image IG so as to be the first respiratory cycle T1, and the plurality of reference frame images RG constituting the reference moving image are each used for the display image IG so as to be the second respiratory cycle T2c.

Figure 24:
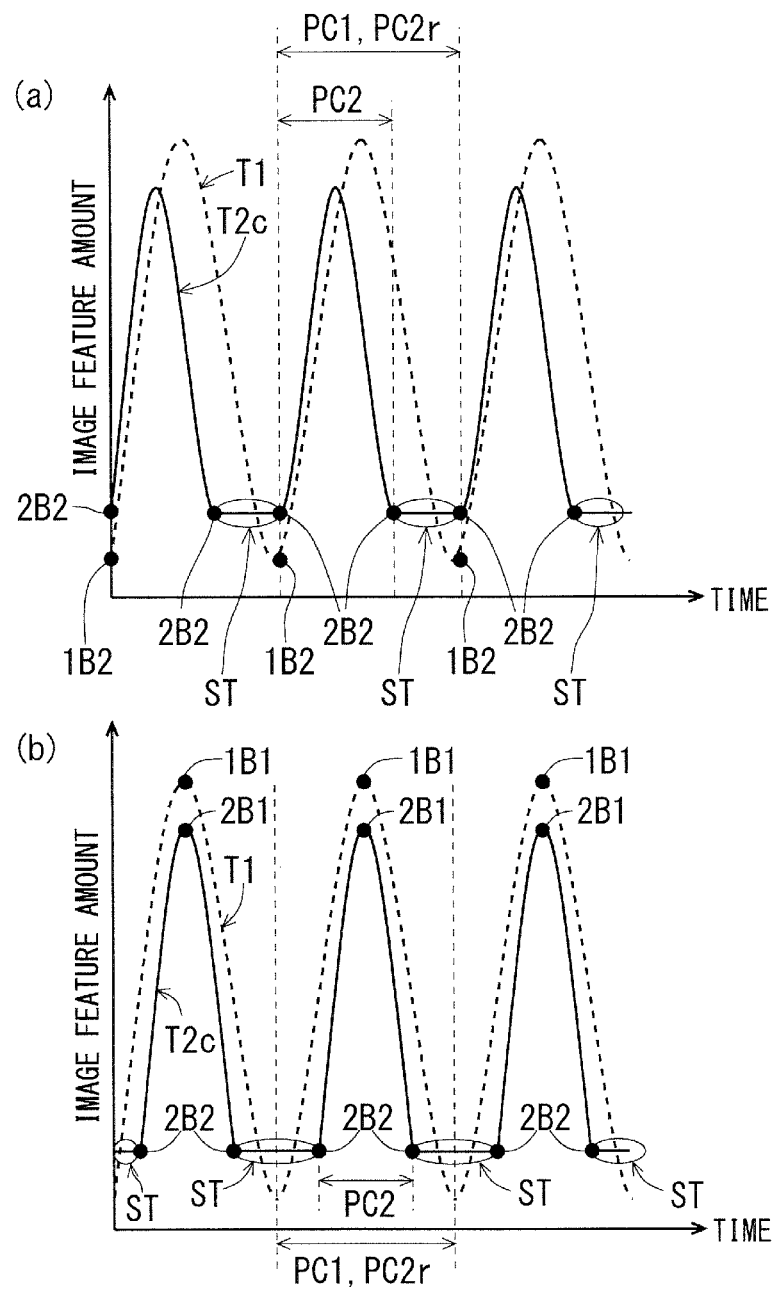
FIG. 24 is a diagram showing examples of first and second lung field region time changes in a display image IG.

FIG. 24 is a diagram showing examples of the first respiratory cycle T1 and the second respiratory cycle T2c in the display image IG. Part (a) of FIG. 24 shows the first respiratory cycle T1 and the second respiratory cycle T2c in the display image IG generated in a case where the period adjusting processing is performed by the adjustment method based on the first feature point. Part (b) of FIG. 24 shows the first respiratory cycle T1 and the second respiratory cycle T2c in the display image IG generated in a case where the period adjusting processing is performed by the adjustment method based on the second feature point.

As shown in parts (a) and (b) of FIG. 24, there are two methods for generating the display image IG. The first generation method is a method of making the difference between the first respiratory period PC1 and the second respiratory period PC2 smaller by causing feature points for adjustment indicating particular phases (the first feature points in this case) used in the period adjusting processing to be continuous in the time direction, as shown in part (a) of FIG. 24. In the case of part (a) of FIG. 24, since the feature points for adjustment are the first feature points, the minimum points 2B2 (first feature points) in the second respiratory cycle T2c are caused to continuously exist within a certain time section ST for each first respiratory period PC1. A second respiratory period PC2r of the second respiratory cycle T2c thus generated matches the first respiratory period PC1, and times required for display of the base moving image and the reference moving image match each other for each first respiratory period PC1. Although part (a) of FIG. 24 shows a case where the feature points for adjustment are the first feature points, the display image IG can also be generated by causing the maximum points 2B1 to be continuous in the time direction in a case where the feature points for adjustment are the second feature points. Furthermore, although part (a) of FIG. 24 shows a case where the second respiratory period PC2 is shorter than the first respiratory period PC1, the reference moving image should be displayed for the duration of the first respiratory period PC1 in a case where the second respiratory period PC2 is longer than the first respiratory period PC1. According to this generation method, a change of a lung field region (target region) starting from the feature points for adjustment used in the period adjusting processing can be observed.

Next, the second method for generating the display image IG is a method of making the difference between the first respiratory period PC1 and the second respiratory period PC2 smaller by causing points (the first feature points in this case) having opposite phases to the feature points for adjustment (the second feature points in this case, i.e., the particular phases) used in the period adjusting processing to be continuous in the time direction, as shown in part (b) of FIG. 24. In the case of part (b) FIG. 24, since the feature points for adjustment are the second feature points, the minimum points 2B2 (first feature points) in the second respiratory cycle T2c are caused to continuously exist within a certain time section ST for each first respiratory period PC1. A second respiratory period PC2r of the second respiratory cycle T2c thus generated matches the first respiratory period PC1, and times required for display of the base moving image and the reference moving image match each other for each first respiratory period PC1. Although part (b) of FIG. 24 shows a case where the feature points for adjustment indicating the particular phases are the second feature points, the display image IG can also be generated by causing the maximum points 2B1 that indicate opposite phases to the second feature points to be continuous in the time direction in a case where the feature points for adjustment are the first feature points. Furthermore, although part (b) of FIG. 24 shows a case where the second respiratory period PC2 is shorter than the first respiratory period PC1, the reference moving image should be displayed for the duration of the first respiratory period PC1 in a case where the second respiratory period PC2 is longer than the first respiratory period PC1. According to this generation method, a change before and after the feature points for adjustment used in the period adjusting processing can be observed.

Display of the reference moving image in the above-mentioned time section ST is in a pause state (display fixed state) on a display of the display unit 34. That is to say, in the examples of parts (a) and (b) of FIG. 24, a reference frame image RG corresponding to the minimum point 2B2 in the second respiratory cycle T2c is continuously displayed during the time section ST.

Although FIG. 24 only shows a case where the period adjusting processing is performed by the adjustment method based on the first and second feature points, the display image IG can be generated by performing similar processing with respect to each feature point in the adjustment methods based on the third to fifth feature points.

As a method for creating the display image IG, the display image IG is created by arranging the base moving image and the reference moving image adjacent to each other. Alternatively, one of the base moving image and the reference moving image may be superimposed onto the other to display these moving images as a single moving image. When displayed through superimposition, these moving images are preferably displayed in different colors. In a case where these moving images are displayed through superimposition, comparison for diagnosis is facilitated, for example, by allocating red and green to the base moving image and the reference moving image, respectively.

Furthermore, visual information may be generated by use of information such as an indicator so that a changed portion (e.g., the above-mentioned time section ST) can be known. For example, in a case where there is a progress bar indicating a current display position during display (playback) of a moving image, a method of displaying the progress bar in color during display of the changed portion can be used, and, in a case where a period diagram is used for display, a method of displaying information before and after change can be used.

<1-3-2. Basic Operation of Image Processing Apparatus 3>

Figure 25:
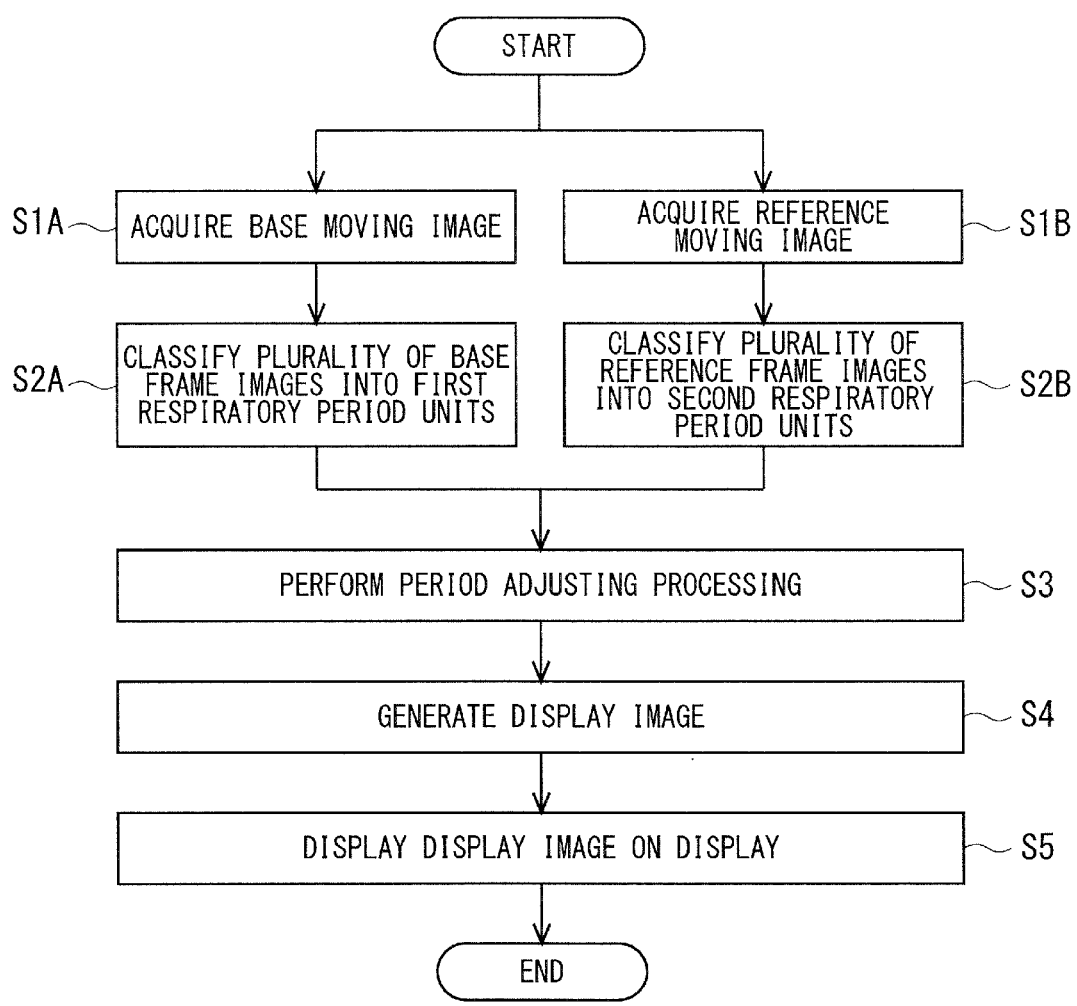
FIG. 25 is a flowchart for explaining a basic operation of the image processing apparatus 3 achieved in Embodiment 1.

FIG. 25 is a flowchart for explaining a basic operation achieved in the image processing apparatus 3 according to the present embodiment. Since an individual function of each unit has already been described (see FIG. 6), only an overall flow is described below.

As shown in FIG. 25, in Step S1A, the base moving image acquiring unit 210 of the control unit 31 first acquires a base moving image (a plurality of base frame images SG) photographed by the reading control device 14 of the imaging apparatus 1 through the photographing control apparatus 2. In Step S1B performed in parallel with Step S1A, the reference moving image acquiring unit 220 of the control unit 31 acquires a reference moving image (a plurality of reference frame images RG) from the reference image storage unit 51 (see FIG. 7).

In Step S2A, the base period extracting unit 310 detects the first respiratory period PC1 based on the first respiratory cycle T1, and classifies the plurality of base frame images SG into first respiratory period PC1 units. In Step S2B performed in parallel with Step S2A, the reference period extracting unit 320 detects the second respiratory period PC2 based on the second respiratory cycle T2, and classifies the plurality of reference frame images RG into second respiratory period PC2 units (see FIGS. 8-18).

In Step S3, the period adjusting unit 400 performs the period adjusting processing of shifting, for each first respiratory period PC1, the second respiratory cycle T2 in the time direction to synchronize the first respiratory cycle T1 and the second respiratory cycle T2 with each other (see FIGS. 20-23).

In Step S4, the display image generating unit 500 generates the display image IG based on the first respiratory cycle T1 and the second respiratory cycle T2c after the period adjusting processing is performed in Step S3, and outputs the display image IG to the display unit 34 (see FIG. 24).

Finally, in Step S5, the display unit 34 displays the display image IG on the display to complete the operation flow.

As described above, the image processing apparatus 3 in Embodiment 1 includes: the period adjusting unit 400 performing the period adjusting processing of synchronizing, for each first respiratory period PC1 or second respiratory period PC2, the periodic changes (first and second respiratory cycles) of the lung field region in the base moving image and in the reference moving image with each other at the particular phase (feature point); and the display image generating unit 500 generating the display image IG allowing for comparison between the base moving image and the reference moving image after the period adjusting processing is performed. That is to say, even in a case where the first respiratory period PC1 and the second respiratory period PC2 differ from each other, display can be achieved so that the particular phases of the first respiratory cycle T1 and the second respiratory cycle T2 match each other for each first respiratory period PC1 or second respiratory period PC2. As a result, a specialist such as a doctor can compare, with reference to the display image IG displayed by the display unit 34, the base moving image and the reference moving image that are synchronized with each other for diagnosis of dynamics, thereby making proper and effective diagnosis of dynamics. In addition, a time for diagnosis through reading of moving images can be reduced, leading to enhancement of users' convenience.

The first respiratory period PC1 or the second respiratory period PC2 is extracted based on at least one of the timings (a1)-(a5), and thus the plurality of base frame images SG or the plurality of reference frame images RG can correctly be classified into the first respiratory period PC1 units or the second respiratory period PC2 units (see FIGS. 14-18).

The period adjusting processing is performed based on a feature point for adjustment (particular phase) that is one of the first to fifth feature points (b1)-(b5), and thus the first respiratory cycle T1 and the second respiratory cycle T2 can correctly be synchronized with each other at the particular phase (see FIGS. 20-23).

The period adjusting processing is performed only by shifting, in the time direction, the timing at which the respiratory cycle to be adjusted becomes the feature point for adjustment so as to match the respiratory cycle to be fixed becomes the feature point for adjustment, and thus the display image IG can be generated with use of changes of the first respiratory cycle T1 and the second respiratory cycle T2 themselves without processing a moving image through image interpolation and the like.

Although the reference moving image is a single moving image in the above-mentioned description, the reference moving image may be two or more moving images. In this case, a base moving image can be compared with a plurality of reference moving images for diagnosis of dynamics.

<2. Embodiment 2>

Figure 26:
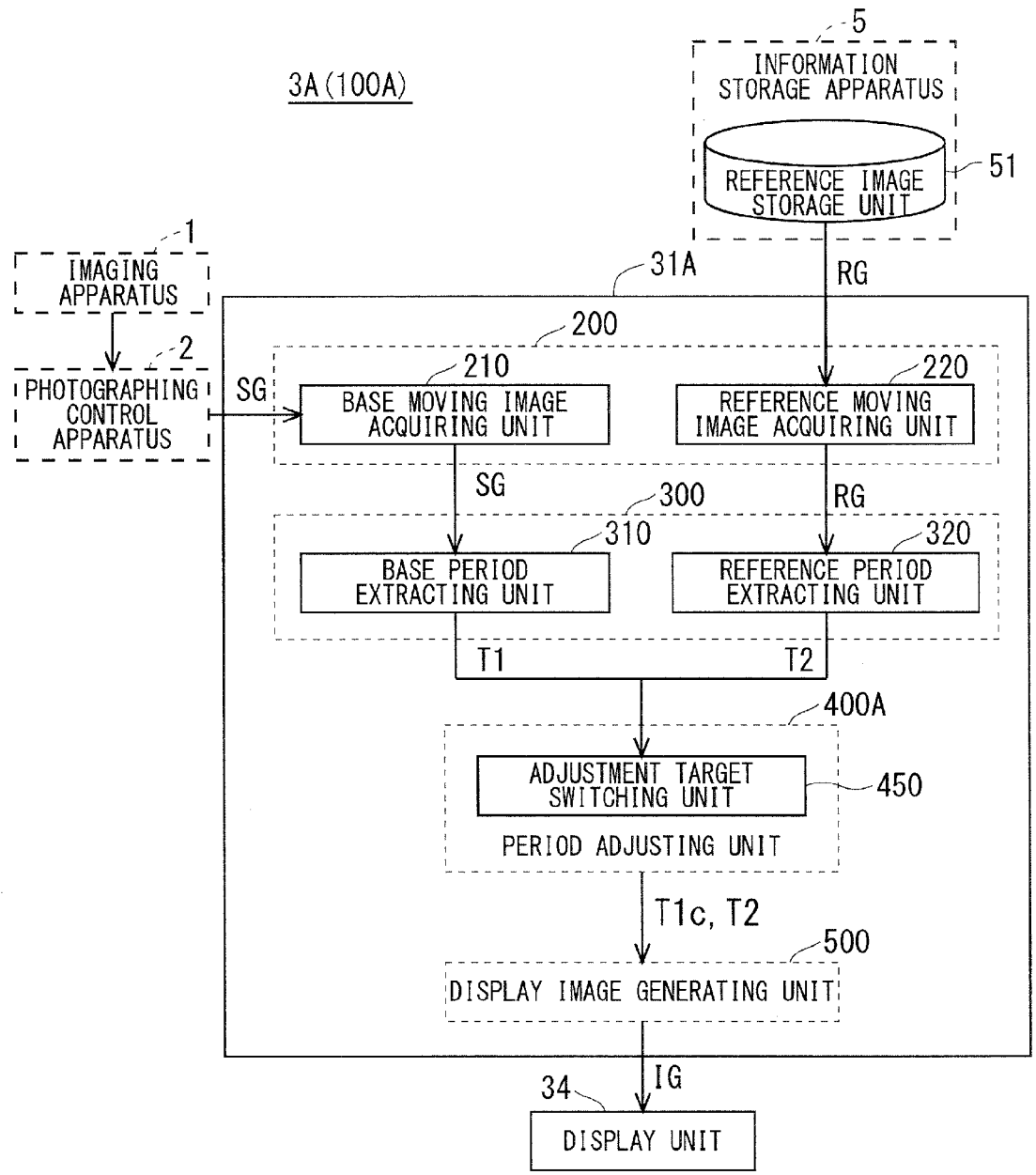
FIG. 26 is a block diagram showing a functional configuration of an image processing apparatus 3A according to Embodiment 2.

FIG. 26 shows a functional configuration of a control unit 31A used in an image processing apparatus 3A configured as Embodiment 2. of the present invention. The control unit 31A is used as a substitute for the control unit 31 (see FIG. 6) in the image processing apparatus 3 in Embodiment 1. This embodiment differs from Embodiment 1 in that a period adjusting unit 400A that corresponds to the period adjusting unit 400 in Embodiment 1. further includes an adjustment target switching unit 450. The remaining configuration is similar to that of the image processing apparatus 3.

<2-1. Adjustment Target Switching Unit 450>

The adjustment target switching unit 450 in the period adjusting unit 400A switches the respiratory cycle to be adjusted between the first respiratory cycle T1 and the second respiratory cycle T2. That is to say, in a case where the respiratory cycle to be adjusted before switching is the second respiratory cycle T2, the adjustment target switching unit 450 can switch the respiratory cycle to be adjusted from the second respiratory cycle T2 to the first respiratory cycle T1, and, in a case where the respiratory cycle to be adjusted before switching is the first respiratory cycle T1, the adjustment target switching unit 450 can switch the respiratory cycle to be adjusted from the first respiratory cycle T1 to the second respiratory cycle T2.

In the case where the base moving image is a newly-photographed moving image as described above, a specialist such as a doctor often observes the base moving image currently targeted for diagnosis while using the reference moving image for reference during reading. Therefore, the display image IG is basically generated by using the base moving image without making any change and by changing display of the reference moving image.

However, it may be useful to use the reference moving image without making any change and to change display of the base moving image to compare these moving images for diagnosis.

In preparation for such a case, the adjustment target switching unit 450 switches the respiratory cycle to be adjusted from the second respiratory cycle T2 in the reference moving image to the first respiratory cycle T1 in the base moving image under user's designation. On the other hand, in a case where the respiratory cycle to be adjusted is to be returned from the first respiratory cycle T1 to the second respiratory cycle T2, the adjustment target switching unit 450 can perform switching under use's designation.

<2-2. Basic Operation of Image Processing Apparatus 3A>

Figure 27:
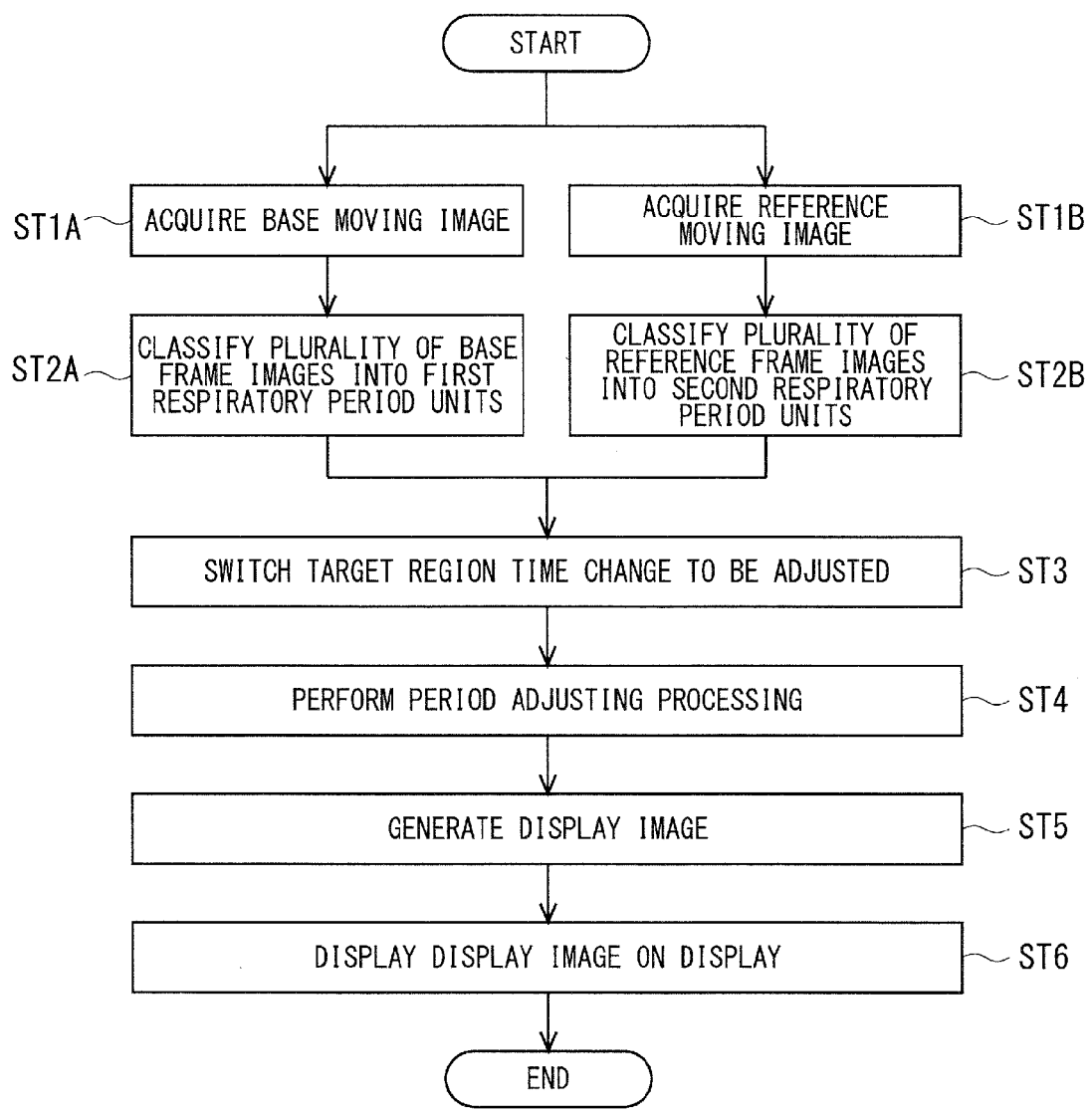
FIG. 27 is a flowchart for explaining a basic operation of the image processing apparatus 3A achieved in Embodiment 2.

FIG. 27 is a diagram showing an example of an operation flow of the image processing apparatus 3A according to Embodiment 2. A default setting of the respiratory cycle to be adjusted is herein the second respiratory cycle T2. Steps ST1A, ST2A, ST1B, ST2B, and ST6 in FIG. 27 are respectively similar to Steps S1A, S2A, S1B, S2B, and S5 in FIG. 25, and thus description thereof is omitted.

In Embodiment 2, the following steps are added by addition of the adjustment target switching unit 450, which does not exist in Embodiment 1.

That is to say, through Steps ST1A, ST2A, ST1B, and ST2B as similar steps to those in Embodiment 1, the adjustment target switching unit 450 switches the respiratory cycle to be adjusted from the second respiratory cycle T2 to the first respiratory cycle T1 in Step ST3 as shown in FIG. 27.

In Step ST4, the period adjusting unit 400A performs the period adjusting processing of shifting, for each second respiratory period PC2, the first respiratory cycle T1 in the time direction to synchronize the base moving image and the reference moving image with each other.

In Step ST5, the display image generating unit 500 generates the display image IG based on the first respiratory cycle T1c and the second respiratory cycle T2 after the period adjusting processing is performed in Step ST4, and outputs the display image IG to the display unit 34 (see FIG. 26). The remaining steps are similar to those in Embodiment 1.

As described above, in the image processing apparatus 3A according to Embodiment 2, a moving image as a target for adjustment can be changed under user's designation by switching the respiratory cycle to be adjusted between the first respiratory cycle T1 and the second respiratory cycle T2.

<3. Embodiment 3>

Figure 28:
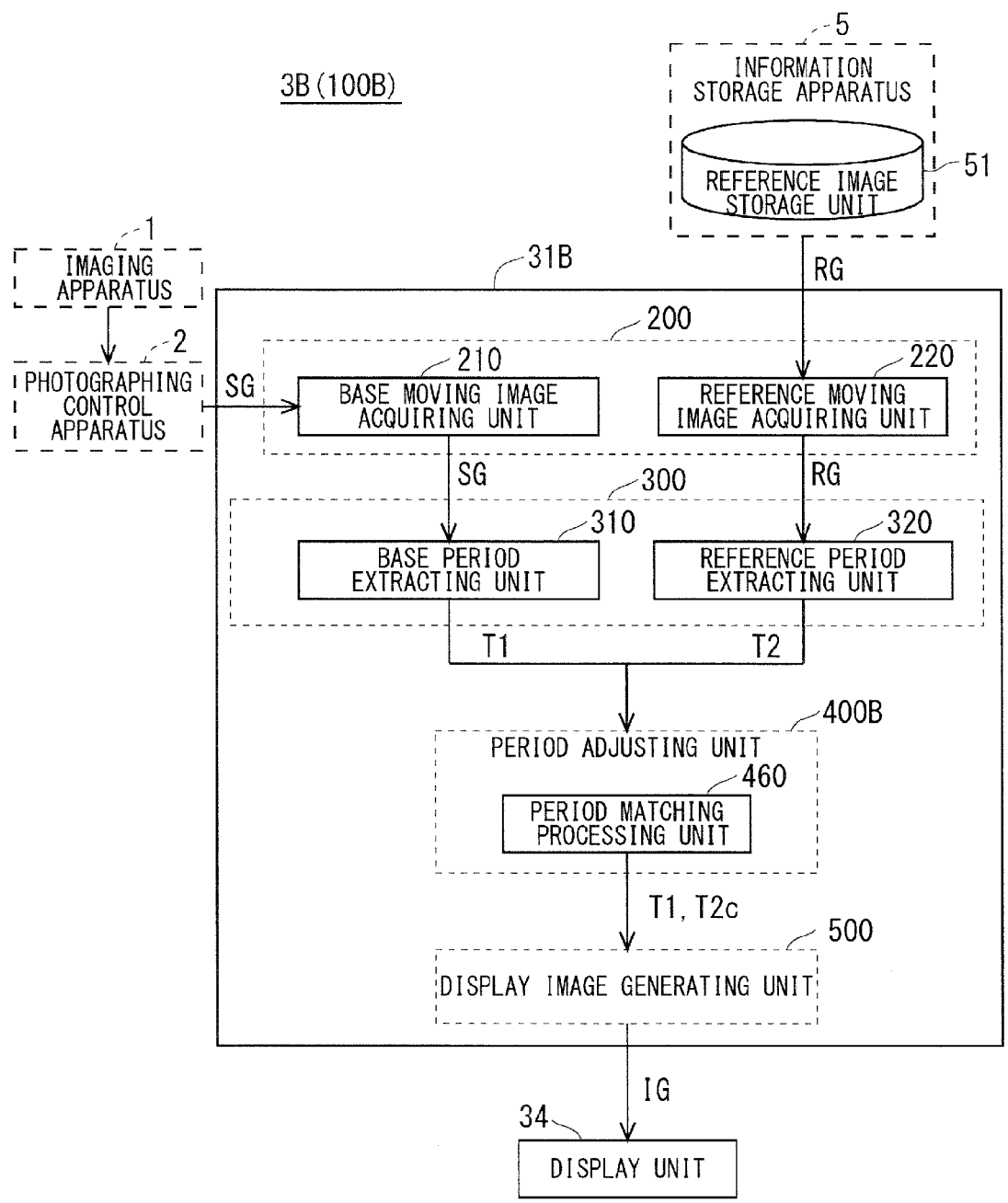
FIG. 28 is a block diagram showing a functional configuration of an image processing apparatus 3B according to Embodiment 3.

FIG. 28 shows a functional configuration of a control unit 31B used in an image processing apparatus 3B configured as Embodiment 3. of the present invention. The control unit 31B is used as a substitute for the control unit 31 (see FIG. 6) in the image processing apparatus 3 in Embodiment 1. This embodiment differs from Embodiment 1 in that a period adjusting unit 400B that corresponds to the period adjusting unit 400 in Embodiment 1. further includes a period matching processing unit 460. The remaining configuration is similar to that of the image processing apparatus 3.

<3-1. Period Matching Processing Unit 460>

The period matching processing unit 460 in the period adjusting unit 400B performs period matching processing of setting one of the first respiratory cycle T1 and the second respiratory cycle T2 as the respiratory cycle to be fixed, setting the other one of the first respiratory cycle T1 and the second respiratory cycle T2 as the respiratory cycle to be adjusted as a target for adjustment, setting a period of the respiratory cycle to be fixed, which is one of the first period PC1 and the second period PC2, as a period to be fixed, setting a period of the respiratory cycle to be adjusted, which is the other one of the first period PC1 and the second period PC2, as a period to be adjusted, and changing the respiratory cycle to be adjusted so that the period to be adjusted matches the period to be fixed. The period matching processing herein is roughly divided into two steps, and each of the steps is described below.

<3-1-1. First Period Matching Processing>

As the first period matching processing, there are two cases described below. As the first case, when the period to be adjusted is shorter than the period to be fixed, the period matching processing is processing of reducing a change speed of the respiratory cycle to be adjusted. In order to reduce the change speed of the respiratory cycle to be adjusted, the number of frame images per unit time (fps: frame per second) during display of a moving image should be reduced. That is to say, a display time of each of frame images constituting the moving image is to be increased.

As the second case, when the period to be adjusted is longer than the period to be fixed, the period matching processing is processing of increasing the change speed of the respiratory cycle to be adjusted. In order to increase the change speed of the respiratory cycle to be adjusted, the number of frame images per unit time during display of a moving image should be increased. That is to say, a display time of each of frame images constituting the moving image is to be reduced. The change speed can also be increased by removing one or more of frame images constituting the moving image.

Figure 29:
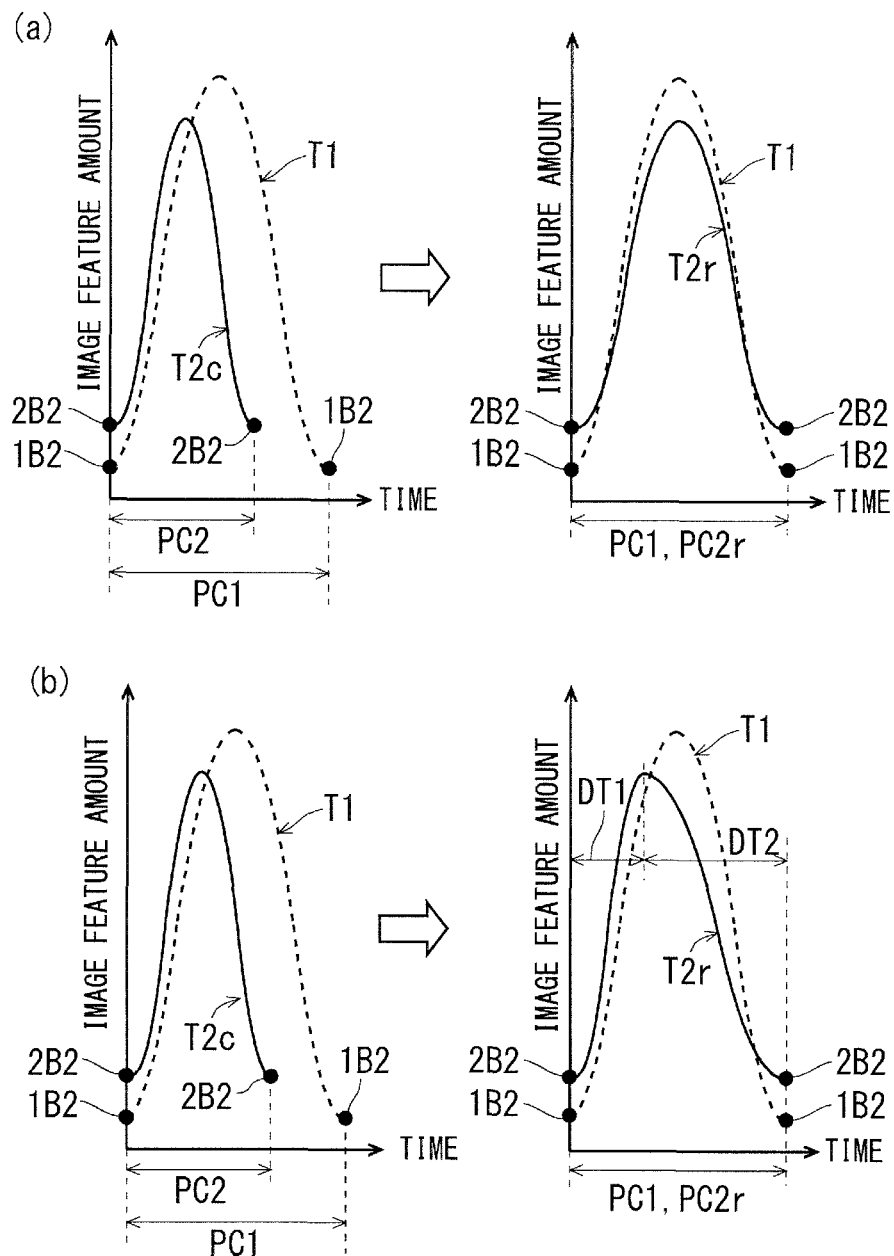
FIG. 29 is a diagram for explaining first period matching processing.

FIG. 29 is a diagram for explaining an example of the first period matching processing with a lung field region as a target region. Parts (a) and (b) of FIG. 29 each show a case where the first respiratory cycle T1 is the respiratory cycle to be fixed, the second respiratory cycle T2 is the respiratory cycle to be adjusted, and the second respiratory period PC2 is shorter than the first respiratory period PC1. That is to say, since the period to be adjusted is shorter than the period to be fixed, the above-mentioned first case is described as an example.

Left diagrams of parts (a) and (b) of FIGS. 29 each show a case where positions, in a time axis direction, of the point 1B2 in the first respiratory cycle T1 and the point 2B2 in the second respiratory cycle T2c are caused to match each other through processing by the period adjustment method performed by the period adjusting unit 400B. Right diagrams of parts (a) and (b) of FIG. 29 each show a case where the second respiratory period PC2r is caused to match the first respiratory period PC1 through processing of reducing the change speed of the second respiratory cycle T2c to generate a second lung field region time change T2r.

A difference between the right diagrams of parts (a) and (b) of FIGS. 29 is described next. That is to say, the right diagrams of parts (a) and (b) of FIG. 29 differ from each other in that, in the right diagram of part (a) of FIG. 29, the processing of reducing the change speed of the second respiratory cycle T2c is performed evenly in the second respiratory period PC2 to generate the second lung field region time change T2r, whereas, in the right diagram of part (b) of FIG. 29, the processing of reducing the change speed is performed only in a particular time section DT2 within the second respiratory period PC2 to generate the second respiratory cycle T2r.

As for the processing of reducing the change speed of the second respiratory cycle T2c, the second respiratory period PC2r can be caused to match the first respiratory period PC1, for example, by changing the change speed of the second respiratory cycle T2r in the right diagram of part (a) of FIG. 29 to an optimal speed such as 7.5 fps when the change speed of the second respiratory cycle T2c in the left diagram of part (a) of FIG. 29 is 15 fps.

As described above, in the first period matching processing, the first respiratory period PC1 and the second respiratory period PC2r are caused to match each other by changing the change speed of frame images.

<3-1-2. Second Period Matching Processing>

The second period matching processing is processing of causing display of a moving image that corresponds to the respiratory cycle to be adjusted to be in a display fixed state during a certain time period when the period to be adjusted is shorter than the period to be fixed. This period matching processing is performed repeatedly for each period to be fixed. Although a time period ST during which display is in the display fixed state is provided after the period to be fixed (a time period between feature points for adjustment in the period adjusting processing) in part (a) of FIG. 24 in Embodiment 1 described above, the time period during which display is in the display fixed state is herein provided within the period to be fixed. Thus, in the example of part (b) of FIG. 24 in Embodiment 1 described above, this period matching processing is performed.

Figure 30:
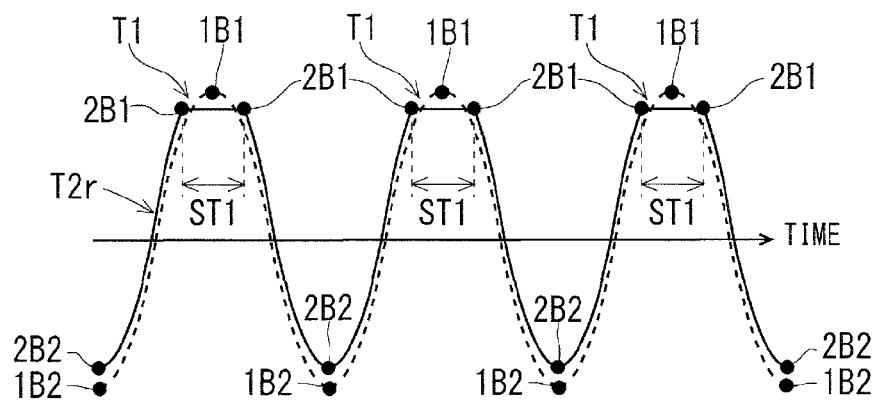
FIG. 30 is a diagram for explaining second period matching processing.

FIG. 30 is a diagram showing the second period matching processing. In FIG. 30, the first respiratory cycle T1 is the respiratory cycle to be fixed, the second respiratory cycle T2 is the respiratory cycle to be adjusted, the first respiratory period PC1 is the period to be fixed, and the second respiratory period PC2 is the period to be adjusted. The second respiratory period PC2 is shorter than the first respiratory period PC1. Through the period adjusting processing described in Embodiment 1 above, the positions, in the time axis direction, of the point 1B2 in the first respiratory cycle T1 and the point 2B2 in the second respiratory cycle T2c are caused to match each other (see part (a) of FIG. 21). Feature points located opposite, in an amplitude direction, the points 2B2 that are the feature points for adjustment used in the period adjusting processing, i.e., the points 2B1 are caused to continuously exist in the time axis direction within the time period ST1. The difference between the first respiratory period PC1 and the second respiratory period PC2 is thereby made smaller. In this case, ST1 =PC1 − PC2 holds. Display of the reference moving image is fixed during the time period ST1. Furthermore, this period matching processing is performed repeatedly for each first respiratory period PC1 as shown in FIG. 30.

Figure 31:
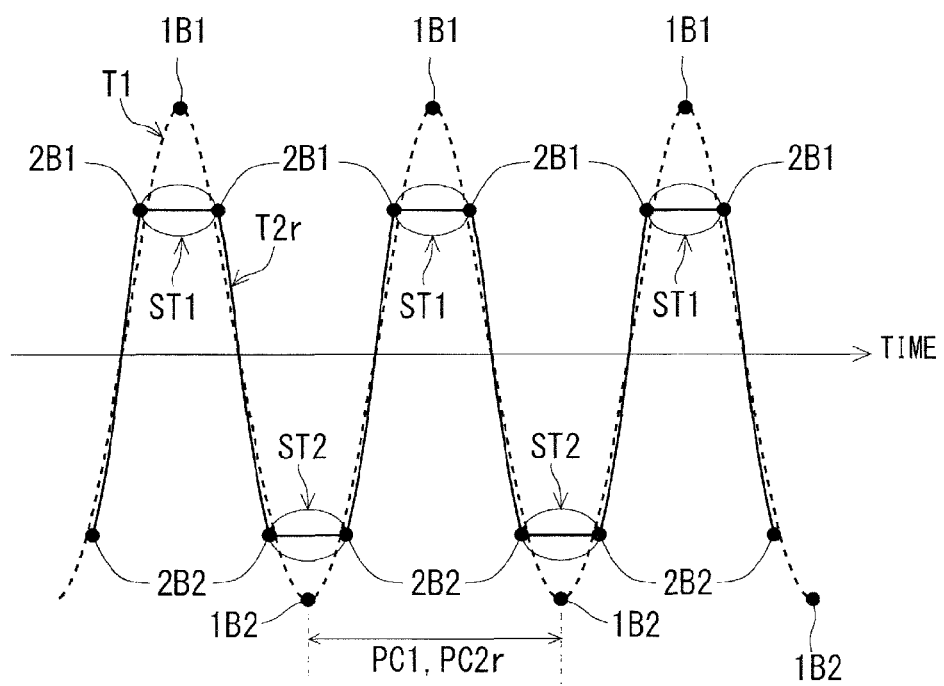
FIG. 31 is a diagram for explaining the second period matching processing.

As described above, in the second period matching processing, the time period ST1 during which display is in the display fixed state is provided within the period to be fixed without changing the display speed (change speed of the first respiratory cycle T1 or the second respiratory cycle T2c) itself As another example of the second period matching processing, both maximum values and minimum values in each respiratory period of the second respiratory cycle may be caused to continuously exist in the time axis direction as shown in FIG. 31. In FIG. 31, the first respiratory cycle T1 is the respiratory cycle to be fixed, the second respiratory cycle T2 is the respiratory cycle to be adjusted, the first respiratory period PC1 is the period to be fixed, and the second respiratory period PC2 is the period to be adjusted, as in FIG. 30. The second respiratory period PC2 is shorter than the first respiratory period PC1. This processing is suitable in a case where the period adjusting processing is performed with use of a point obtained from an inflection point of the respiratory cycle (see FIG. 16), a predetermined threshold (see FIG. 17), and the absolute value of an inclination (see FIG. 18). When the period adjusting processing is performed with used of such a point, phases can be caused to match each other by using an intermediate image feature amount between a maximum value (time of maximum inhalation) and a minimum value (time of maximum exhalation) in each respiratory period, and thus it is easy to cause display to be in the display fixed state at the maximum value (time of maximum inhalation) and at the minimum value (time of maximum exhalation). In FIG. 31, for each period to be fixed, maximum values 2B1 and minimum values 2B2 of the second respiratory cycle are caused to continuously exist within the time periods ST1 and ST2, respectively, to cause the reference moving image to be in the display fixed state within these time periods.

<3-2. Basic Operation of Image Processing Apparatus 3B>

Figure 32:
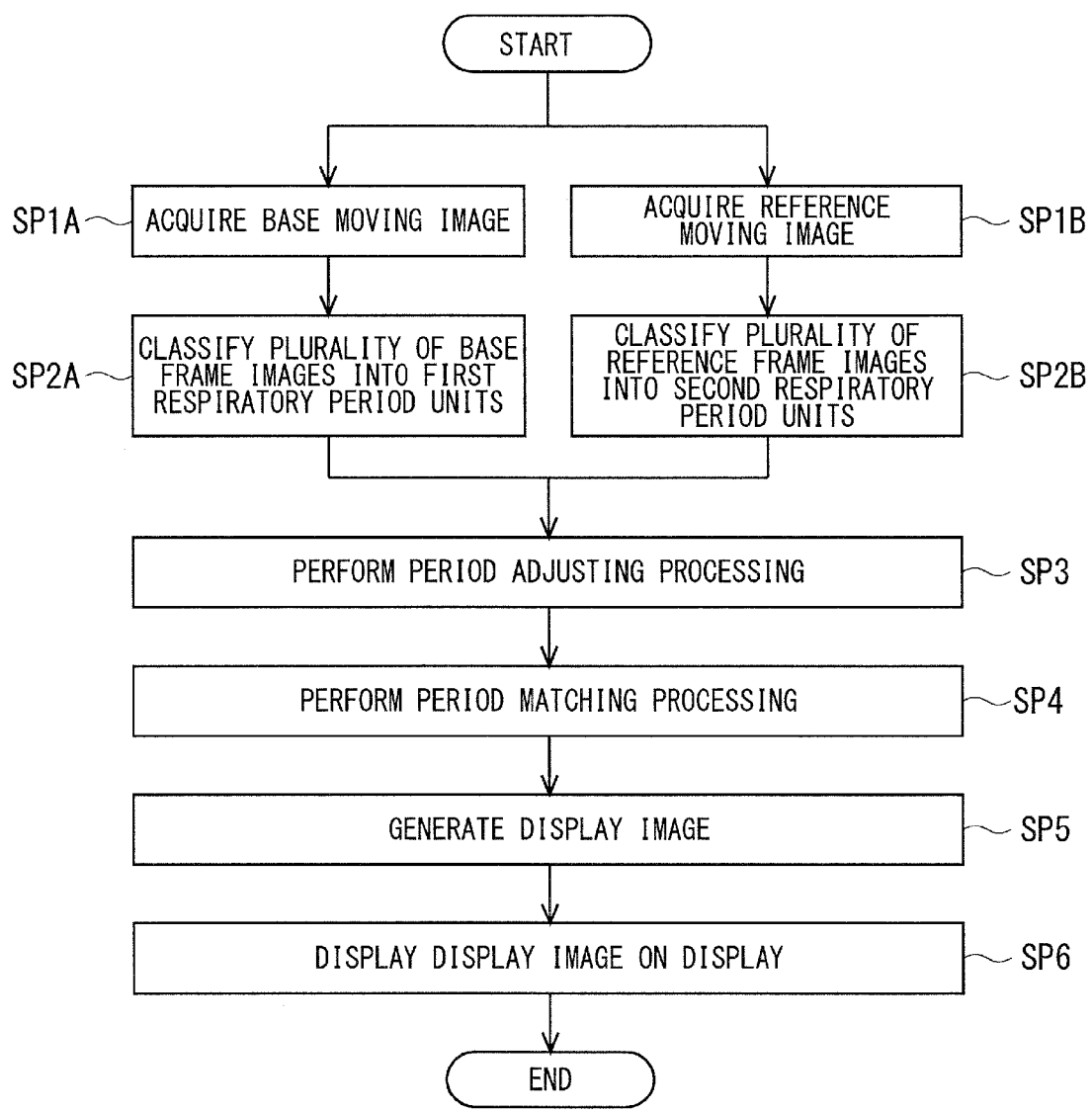
FIG. 32 is a flowchart for explaining a basic operation of the image processing apparatus 3B achieved in Embodiment 3.

FIG. 32 is a diagram showing an example of an operation flow of the image processing apparatus 3B according to Embodiment 3. Herein, the first respiratory cycle T1 is the respiratory cycle to be fixed, the second respiratory cycle T2 is the respiratory cycle to be adjusted, the first respiratory period PC1 is the period to be fixed, and the second respiratory period PC2 is the period to be adjusted. Steps SP1A, SP2A, SP1B, SP2B, SP3, SP5, and SP6 in FIG. 32 are respectively similar to Steps S1A, S2A, S1B, S2B, S3, S5, and S6 in FIG. 25, and thus description thereof is omitted.

That is to say, through Steps SP1A, SP2A, SP1B, SP2B, and SP3 as similar steps to those in Embodiment 1, the period matching processing unit 460 changes the second respiratory cycle T2c so that the second respiratory period PC2 matches the first respiratory period PC1 through the above-mentioned first or second period matching processing to generate the second respiratory cycle T2r in Step SP4 as shown in FIG. 32 (see FIGS. 29-31). The remaining steps are similar to those in Embodiment 1.

As described above, in the image processing apparatus 3B according to Embodiment 3, the period adjusting processing includes period matching processing of changing the second respiratory cycle T2c (respiratory cycle to be adjusted) so that the second respiratory period PC2 (period to be adjusted) matches the first respiratory period PC1 (period to be fixed). As a result, the display image IG can be generated only by adjusting the display time in the second respiratory period PC2 without adjusting the display time in the first respiratory period PC1.

According to Embodiment 3, continuous display of the second respiratory cycle T2r and continuous display of the first respiratory cycle T1 can be achieved in such a manner that these cycles can easily be identified for comparison for each first respiratory period PC1.

<4. Modifications>

While the embodiments of the present invention have been described so far, the present invention is not limited to the above-mentioned embodiments, and may be variously modified.

For example, Embodiments 1-3. above describe cases where periodic movement of the target region in the base moving image and in the reference moving image is the respiratory cycle of the lung field region, but it may be heart rate information (heart rate cycle) of a heart region. That is to say, the heart rate cycle may be used in place of the respiratory cycle. A method for detecting the heart rate cycle and a method for detecting a heart rate period in that case are described below.

<4-1. First Method for Detecting Change (Heart Rate Cycle) of Heart Region>

As a first method for detecting a heart rate cycle, as described in FIG. 6, the base period extracting unit 310 calculates a movement amount of a cardiac wall with use of a plurality of base frame images SG acquired by the base moving image acquiring unit 210 to generate a first heart rate cycle T1 (heart rate information), and the reference period extracting unit 320 calculates a movement amount of a cardiac wall with use of a plurality of reference frame images RG acquired by the reference moving image acquiring unit 220 to generate a second heart rate cycle T2 (heart rate information).

Specifically, by detecting a change of the cardiac wall from the moving image, a phase of pulsation of the heart at a timing of photographing each frame image SG (RG) is detected. The cardiac wall is thus detected as the phase of pulsation of the heart.

FIG. 11 is a schematic diagram illustrating the change of the cardiac wall captured in a moving image. As illustrated in FIG. 11, a change of the width of the heart is used as an example of the change of a cardiac wall HL. Parts (a) to (c) of FIG. 11 illustrate states in which the width of the heart increases from w1 to w3 in the course of expansion of the heart.

The base period extracting unit 310 (reference period extracting unit 320) detects the width of the heart from each frame image SG (RG) to generate the first (second) heart rate cycle T1 (T2). One specific example of a technique for detecting the width of the heart is a technique of detecting the contour of the heart. Various known techniques can be used as the technique of detecting the contour of the heart, and, for example, a technique of detecting the contour of the heart by fitting, with use of a model showing the shape of the heart (heart model), feature points in an X-ray image and feature points in the heart model (for example, see "Image feature analysis and computer-aided diagnosis in digital radiography: Automated analysis of sizes of heart and lung in chest images", Nobuyuki Nakamori et al., Medical Physics, Volume 17, Issue 3, May, 1990, pp. 342-350) can be used.

FIG. 12 is a schematic diagram showing the relationship between a photographing time and the width of the heart for the plurality of base frame images SG constituting the base moving image (plurality of reference frame images RG constituting the reference moving image). In FIG. 12, the horizontal and vertical axes represent time and the width of the heart, respectively, and circles represent values of the width of the heart as detected.

Here, Hw(t) and Hw(t+1) denote the width of the heart captured at a time t and the width of the heart captured at a time (t+1), respectively, and, if(Hw(t+1)−Hw(t))≥0 holds, a frame image SG (RG) captured at the time t is classified as a frame image during expansion of the heart, and, if (Hw (t+1)−Hw(t))<0. holds, the frame image SG (RG) captured at the time t is classified as a frame image during contraction of the heart.

As described above, frame images can be classified into frame images during expansion of the heart and frame images during contraction of the heart by detecting the change of the width of the heart, namely, the change of the cardiac wall HL, so that the phase of pulsation of the heart can be detected, and the heart rate cycle (curve) can be obtained.

<4-2. Second Method for Detecting Change (Heart Rate Cycle) of Heart Region>

As a second method for detecting a heart region time change, measurement results of an electrocardiograph are used. That is to say, this detection method can be used when heart rate information is acquired from an outside source in synchronization with photographing of a plurality of base frame images SG (or a plurality of reference frame images RG). FIG. 13 shows an example of a partial electrocardiograph waveform of the test subject M. In FIG. 13, the horizontal and vertical axes represent time and the magnitude of an electrical signal (voltage), respectively, and a curve showing a change of the electrical signal including curves Pp, Qp, Rp, Sp, Tp, and Up respectively showing shapes of so-called P, Q, R, S, T, and U waves is shown.

Since the electrocardiograph 4 is provided in the system configuration of FIG. 1, an output of the electrocardiograph 4 can be used. In this case, the base period extracting unit 310 acquires the plurality of base frame images SG through the base moving image acquiring unit 210, and also acquires the heart rate information synchronized with the plurality of base frame images SG to set the heart rate information as the first heart rate cycle T1. On the other hand, the reference period extracting unit 320 acquires the plurality of reference frame images RG as well as the heart rate information synchronized with the plurality of reference frame images RG from the reference image storage unit 51 through the reference moving image acquiring unit 220 to set the heart rate information as the second heart rate cycle T2. As for the reference moving image, it is assumed that the heart rate information is acquired by the electrocardiograph 4 at the time of photographing the reference moving image, and the heart rate information is stored in the reference image storage unit 51 in association with the reference moving image.

Even in a case where the heart rate cycle is used, similar period adjusting processing and display image generating processing to those performed in a case where the respiratory cycle is used can be used.

<4-3. Heart Rate Period Detection Method>

The method for detecting the heart rate period of the first (second) heart rate cycle T1 (T2) is described next.

With respect to the heart rate cycle T1 (T2) (corresponding to the movement of the cardiac wall shown in FIG. 12) detected by the first method for detecting the heart rate cycle, the heart rate period can be detected based on any of or a combination of the timings (a1) to (a6) described concerning the above-mentioned respiratory cycle.

The same applies to the heart rate cycle T1 (T2) detected by the second method for detecting the heart rate cycle, and, in this detection method, the heart rate period can easily be detected based on the points (Pp, Qp, Rp, Sp, Tp, and Up) acquired from the phase detecting unit 41 shown in FIG. 13. The plurality of base frame images SG or reference frame images RG can then be classified into first heart rate period PC1 units or second heart rate period PC2 units.

<4-4. Others>

Although the Image Processing Apparatuses 3, 3A, and 3B are Described Separately in the Above-Mentioned Embodiments so as to be Implemented Individually, Individual Functions of the Image Processing Apparatuses 3, 3A, and 3B may be Combined With One Another Unless any Contradiction Occurs.

The subject is not limited to the human body, and may be the body of an animal.

While the present invention has been described in detail, the foregoing description is in all aspects illustrative and not restrictive. It is therefore understood that numerous modifications that have not been described can be devised without departing from the scope of the present invention.

The invention claimed is:

1. An image processing apparatus comprising:
a base moving image acquiring unit acquiring a base moving image in which a periodic change of a physical state of a target region of a human body or an animal is captured;
a reference moving image acquiring unit acquiring a reference moving image in which a periodic change of a physical state of said target region of a human body or an animal is captured, said reference moving image being to be compared with said base moving image;
a base period extracting unit extracting a first target region period based on a first periodic change that is a periodic change of said target region in said base moving image;
a reference period extracting unit extracting a second target region period based on a second periodic change that is a periodic change of said target region in said reference moving image;
a period adjusting unit performing period adjusting processing of synchronizing, for each said first target region period or said second target region period, said first periodic change and said second periodic change with each other at a particular phase; and
a display image generating unit generating a display image allowing for comparison between said base moving image and said reference moving image after said period adjusting processing is performed, wherein when said first target region period and said second target region period differ from each other, said display image generating unit causes display of said base moving image or said reference moving image that corresponds to a shorter one of said first target region period and said second target region period to be in a fixed state during a time period corresponding to a difference between said first target region period and said second target region period.

2. The image processing apparatus according to claim 1, wherein said display image generating unit causes said display of said base moving image or said reference moving image to be in said fixed state at said particular phase.

3. The image processing apparatus according to claim 1, wherein said display image generating unit causes said display of said base moving image or said reference moving image to be in said fixed state at an opposite phase to said particular phase.

4. The image processing apparatus according to claim 1, wherein said period adjusting unit shifts, for each said first target region period, said second periodic change in a time axis direction so that said second periodic change is at said particular phase when said first periodic change is at said particular phase.

5. The image processing apparatus according to claim 1, wherein said period adjusting unit sets one of said first periodic change and said second periodic change as a periodic change to be fixed, sets the other one of said first periodic change and said second periodic change as a periodic change to be adjusted, and shifts said periodic change to be adjusted in a time axis direction so that said periodic change to be adjusted is at said particular phase when said periodic change to be fixed is at said particular phase, and
comprises an adjustment target switching unit switching said periodic change to be adjusted between said first periodic change and said second periodic change.

6. The image processing apparatus according to claim 1, wherein said first target region period or said second target region period is extracted based on at least one of:
(a1) at least one of a timing showing a minimum value of said periodic change of said target region within a reference time period and a timing showing a maximum value of said periodic change of said target region within said reference time period;
(a2) a timing showing a change point at which a positive or negative sign of an inclination of a curve showing said periodic change of said target region changes;
(a3) a timing showing an inflection point of said curve showing said periodic change of said target region;
(a4) a timing showing a point at which a value showing said periodic change of said target region becomes a predetermined threshold; and
(a5) a timing showing a point at which an absolute value of said inclination of said curve showing said periodic change of said target region exceeds a reference value.

7. The image processing apparatus according to claim 1, wherein said period adjusting processing is performed, for each said first target region period and said second target region period, based on a feature point for adjustment that is any one of:
(b1) a first feature point at which said periodic change of said target region in said base moving image and said reference moving image is smallest;
(b2) a second feature point at which said periodic change of said target region in said base moving image and said reference moving image is the largest;
(b3) a third feature point that is an inflection point of a curve showing said periodic change of said target region in said base moving image and said reference moving image;
(b4) a fourth feature point at which a value showing said periodic change of said target region in said base moving image and said reference moving image becomes a predetermined threshold; and
(b5) a fifth feature point at which an absolute value of an inclination of said curve showing said periodic change of said target region in said base moving image and said reference moving image is highest.

8. The image processing apparatus according to claim 1, wherein said reference moving image includes two or more moving images.

9. The image processing apparatus according to claim 1, wherein said target region is a lung.

10. The image processing apparatus according to claim 1, further comprising a display unit displaying said display image.

11. An image processing apparatus comprising:
a base moving image acquiring unit acquiring a base moving image in which a periodic change of a physical state of a target region of a human body or an animal is captured;
a reference moving image acquiring unit acquiring a reference moving image in which a periodic change of a physical state of said target region of a human body or an animal is captured, said reference moving image being to be compared with said base moving image;
a base period extracting unit extracting a first target region period based on a first periodic change that is a periodic change of said target region in said base moving image;
a reference period extracting unit extracting a second target region period based on a second periodic change that is a periodic change of said target region in said reference moving image;
a period adjusting unit performing period adjusting processing of synchronizing, for each said first target region period or said second target region period, said first periodic change and said second periodic change with each other at a particular phase, wherein said period adjusting unit comprises a period matching processing unit reducing, when said first target region period and said second target region period differ from each other, a change speed of said first periodic change or said second periodic change that corresponds to a shorter one of said first target region period and said second target region period; and
a display image generating unit generating a display image allowing for comparison between said base moving image and said reference moving image after said period adjusting processing is performed.

12. An image processing apparatus comprising:
a base moving image acquiring unit acquiring a base moving image in which a periodic change of a physical state of a target region of a human body or an animal is captured;
a reference moving image acquiring unit acquiring a reference moving image in which a periodic change of a physical state of said target region of a human body or an animal is captured, said reference moving image being to be compared with said base moving image;
a base period extracting unit extracting a first target region period based on a first periodic change that is a periodic change of said target region in said base moving image;
a reference period extracting unit extracting a second target region period based on a second periodic change that is a periodic change of said target region in said reference moving image;

a period adjusting unit performing period adjusting processing of synchronizing, for each said first target region period or said second target region period, said first periodic change and said second periodic change with each other at a particular phase, wherein said period adjusting unit comprises a period matching processing unit increasing, when said first target region period and said second target region period differ from each other, a change speed of said first periodic change or said second periodic change that corresponds to longer one of said first target region period and said second target region period; and a display image generating unit generating a display image allowing for comparison between said base moving image and said reference moving image after said period adjusting processing is performed.

13. An image processing method comprising:

acquiring a base moving image in which a periodic change of a physical state of a target region of a human body or an animal is captured;

acquiring a reference moving image in which a periodic change of a physical state of said target region of a human body or an animal is captured, said reference moving image being to be compared with said base moving image;

extracting a first target region period based on a first periodic change that is a periodic change of said target region in said base moving image;

extracting a second target region period based on a second periodic change that is a periodic change of said target region in said reference moving image;

performing period adjusting processing of synchronizing, for each said first target region period or said second target region period, said first periodic change and said second periodic change with each other at a particular phase; and generating a display image allowing for comparison between said base moving image and said reference moving image after said period adjusting processing is performed, wherein when said first target region period and said second target region period differ from each other, said generating a display image causes display of said base moving image or said reference moving image that corresponds to shorter one of said first target region period and said second target region period to be in a fixed state during a time period corresponding to a difference between said first target region period and said second target region period.

14. The image processing method according to claim 13, wherein said performing period adjusting processing of synchronizing shifts, for each said first target region period, said second periodic change in a time axis direction so that said second periodic change is at said particular phase when said first periodic change is at said particular phase.

15. The image processing method according to claim 13, wherein said performing period adjusting processing of synchronizing sets one of said first periodic change and said second periodic change as a periodic change to be fixed, sets the other one of said first periodic change and said second periodic change as a periodic change to be adjusted, and shifts said periodic change to be adjusted in a time axis direction so that said periodic change to be adjusted is at said particular phase when said periodic change to be fixed is at said particular phase, and comprising switching said periodic change to be adjusted between said first periodic change and said second periodic change.

16. The image processing method according to claim 13, wherein said first target region period or said second target region period is extracted based on at least one of:

(a1) at least one of a timing showing a minimum value of said periodic change of said target region within a reference time period and a timing showing a maximum value of said periodic change of said target region within said reference time period;

(a2) a timing showing a change point at which a positive or negative sign of an inclination of a curve showing said periodic change of said target region changes;

(a3) a timing showing an inflection point of said curve showing said periodic change of said target region;

(a4) a timing showing a point at which a value showing said periodic change of said target region becomes a predetermined threshold; and (a5) a timing showing a point at which an absolute value of said inclination of said curve showing the periodic change of said target region exceeds a reference value.

17. The image processing method according to claim 13, wherein said period adjusting processing is performed, for each said first target region period and said second target region period, based on a feature point for adjustment that is any one of:

(b1) a first feature point at which said periodic change of said target region in said base moving image and said reference moving image is smallest;

(b2) a second feature point at which said periodic change of said target region in said base moving image and said reference moving image is largest;

(b3) a third feature point that is an inflection point of a curve showing said periodic change of said target region in said base moving image and said reference moving image;

(b4) a fourth feature point at which a value showing said periodic change of said target region in said base moving image and said reference moving image becomes a predetermined threshold; and (b5) a fifth feature point at which an absolute value of an inclination of said curve showing said periodic change of said target region in said base moving image and said reference moving image is highest.

18. An image processing method comprising:

acquiring a base moving image in which a periodic change of a physical state of a target region of a human body or an animal is captured;

acquiring a reference moving image in which a periodic change of a physical state of said target region of a human body or an animal is captured, said reference moving image being to be compared with said base moving image;

extracting a first target region period based on a first periodic change that is a periodic change of said target region in said base moving image;

extracting a second target region period based on a second periodic change that is a periodic change of said target region in said reference moving image;

performing period adjusting processing of synchronizing, for each said first target region period or said second target region period, said first periodic change and said second periodic change with each other at a particular phase, wherein said performing period adjusting processing of synchronizing comprises reducing, when said first target region period and said second target region period differ from each other, a change speed of said first periodic change or said second periodic change that corresponds to a shorter one of said first target region period and said second target region period; and
a display image generating step generating a display image allowing for comparison between said base moving image and said reference moving image after said period adjusting processing of synchronizing is performed.

19. An image processing method comprising:

acquiring a base moving image in which a periodic change of a physical state of a target region of a human body or an animal is captured;

acquiring a reference moving image in which a periodic change of a physical state of said target region of a human body or an animal is captured, said reference moving image being to be compared with said base moving image;

extracting a first target region period based on a first periodic change that is a periodic change of said target region in said base moving image;

extracting a second target region period based on a second periodic change that is a periodic change of said target region in said reference moving image;

performing period adjusting processing of synchronizing, for each said first target region period or said second target region period, said first periodic change and said second periodic change with each other at a particular phase, wherein said performing period adjusting processing of synchronizing comprises increasing, when said first target region period and said second target region period differ from each other, a change speed of said first periodic change or said second periodic change that corresponds to a longer one of said first target region period and said second target region period; and a display image generating step generating a display image allowing for comparison between said base moving image and said reference moving image after said period adjusting processing of synchronizing is performed.

\* \* \* \* \*